(12) United States Patent
Weiss et al.

(10) Patent No.: US 10,265,519 B2
(45) Date of Patent: Apr. 23, 2019

(54) RADIO FREQUENCY ABLATION CATHETER AND MAGNETIC RESONANCE IMAGING SYSTEM

(75) Inventors: Steffen Weiss, Hamburg (DE); Sascha Krueger, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 13/503,084

(22) PCT Filed: Oct. 25, 2010

(86) PCT No.: PCT/IB2010/054816
§ 371 (c)(1),
(2), (4) Date: Apr. 20, 2012

(87) PCT Pub. No.: WO2011/051872
PCT Pub. Date: May 5, 2011

(65) Prior Publication Data
US 2012/0203100 A1  Aug. 9, 2012

(30) Foreign Application Priority Data
Nov. 2, 2009 (EP) .................................... 09174740

(51) Int. Cl.
| *A61N 1/06* | (2006.01) |
| *A61B 5/042* | (2006.01) |
| *A61B 18/14* | (2006.01) |
| *G01R 33/28* | (2006.01) |
| *A61B 17/00* | (2006.01) |
| *A61B 18/00* | (2006.01) |

(Continued)

(52) U.S. Cl.
CPC .............. *A61N 1/06* (2013.01); *A61B 5/0422* (2013.01); *A61B 18/1492* (2013.01); *G01R 33/285* (2013.01); *G01R 33/288* (2013.01); *A61B 2017/00084* (2013.01); *A61B 2018/00023* (2013.01); *A61B 2018/00029* (2013.01); *A61B 2018/00791* (2013.01); *A61B 2090/374* (2016.02); *A61N 1/086* (2017.08)

(58) Field of Classification Search
USPC ...................... 600/410, 411, 412, 423; 601/2
See application file for complete search history.

(56) References Cited

U.S. PATENT DOCUMENTS

| 5,599,346 A * | 2/1997 | Edwards et al. ................ 606/41 |
| 6,280,441 B1 * | 8/2001 | Ryan ............................... 606/45 |

(Continued)

FOREIGN PATENT DOCUMENTS

WO    2009004548 A2    1/2009

OTHER PUBLICATIONS

Ladd M E et al. "Reduction of Resonant RF Heating in Intravascular Catheters Using Coaxial Chokes". Magnetic in Resonance Medicine, academic Press, Duluth, MN. vol. 43, No. 4, Jan. 1, 2000, pp. 615-619.

(Continued)

*Primary Examiner* — Katherine Fernandez

(57) ABSTRACT

A catheter comprising: —a transmission line (104, 106, 924, 1202, 1302, 1902), wherein the transmission line comprises a plurality of radio frequency traps (118, 318, 418, 518, 618, 718, 818, 918, 1018, 1202, 1404); and —a cooling line (104, 304, 1200, 1900) for cooling the plurality of radio frequency traps with a fluid.

17 Claims, 14 Drawing Sheets

(51) Int. Cl.
*A61B 90/00* (2016.01)
*A61N 1/08* (2006.01)

(56) References Cited

U.S. PATENT DOCUMENTS

| | | | |
|---|---|---|---|
| 6,580,274 B2* | 6/2003 | Sato | 324/318 |
| 7,388,378 B2 | 6/2008 | Gray et al. | |
| 7,561,906 B2 | 7/2009 | Atalar et al. | |
| 7,742,799 B2* | 6/2010 | Mueller et al. | 600/410 |
| 2004/0046557 A1* | 3/2004 | Karmarkar et al. | 324/322 |
| 2004/0220470 A1* | 11/2004 | Karmarkar et al. | 600/423 |
| 2005/0251031 A1 | 11/2005 | Smith | |
| 2006/0252314 A1* | 11/2006 | Atalar et al. | 439/876 |
| 2008/0143459 A1* | 6/2008 | Vernickel | A61N 1/3718 333/24 C |
| 2008/0154346 A1 | 6/2008 | Smith et al. | |
| 2009/0118610 A1* | 5/2009 | Karmarkar | A61B 5/0476 600/420 |
| 2009/0171421 A1 | 7/2009 | Atalar et al. | |
| 2011/0054582 A1* | 3/2011 | Dabney | A61N 1/056 607/116 |
| 2011/0077635 A1* | 3/2011 | Bonn | 606/33 |

OTHER PUBLICATIONS

Weiss S et al. "Transmission Line for Improved RF Safety of Interventional Devices". Magnetic Resonance in Medicine, Academic Press, Duluth, MN. vol. 54, Jan. 1, 2005, pp. 182-189.

* cited by examiner

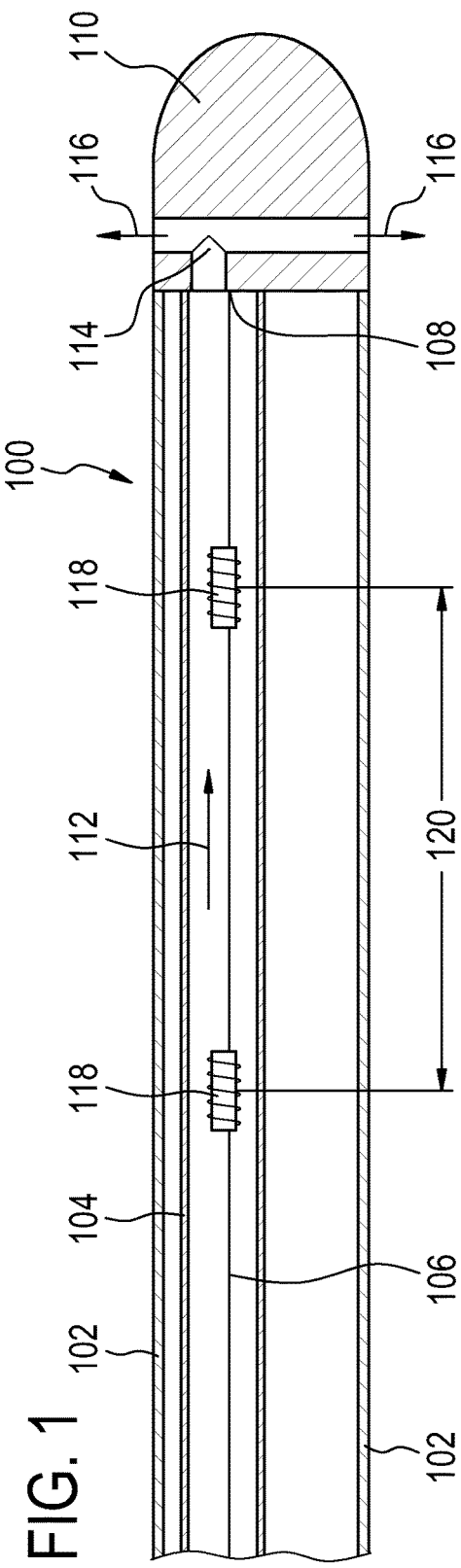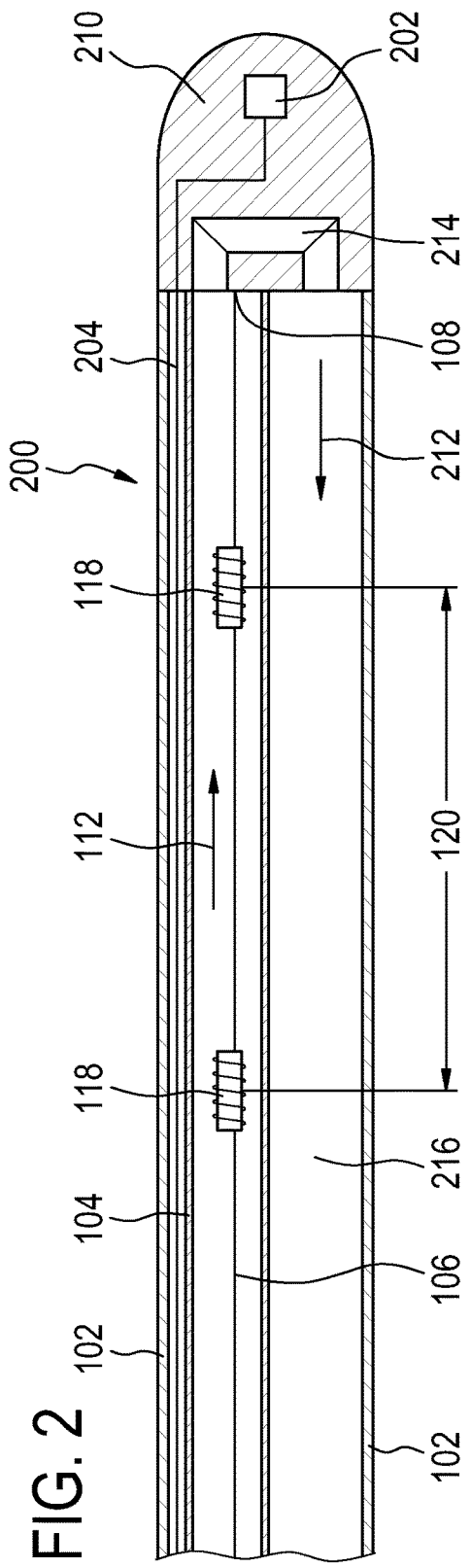

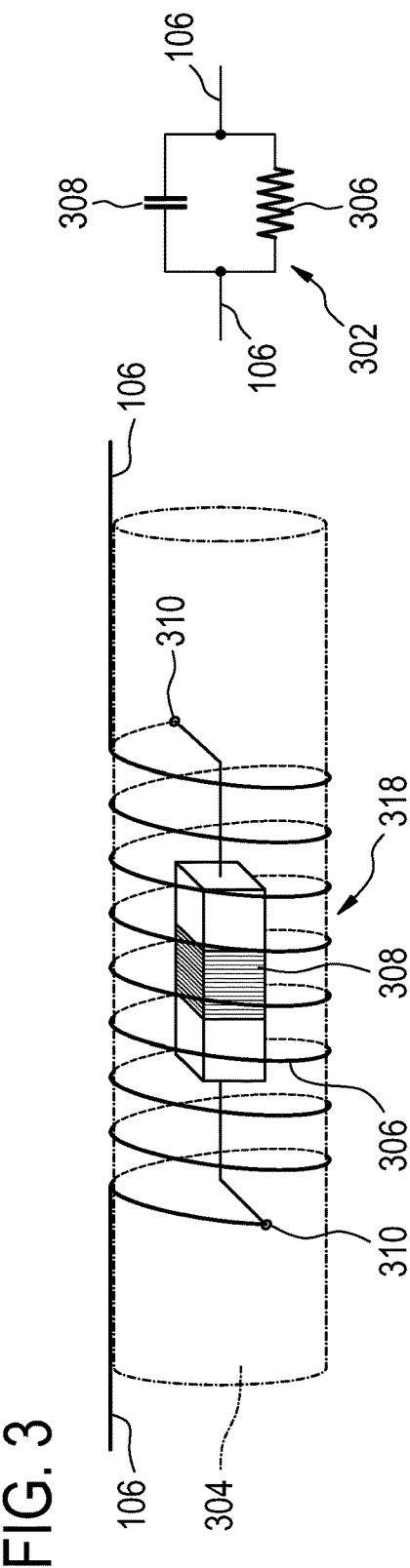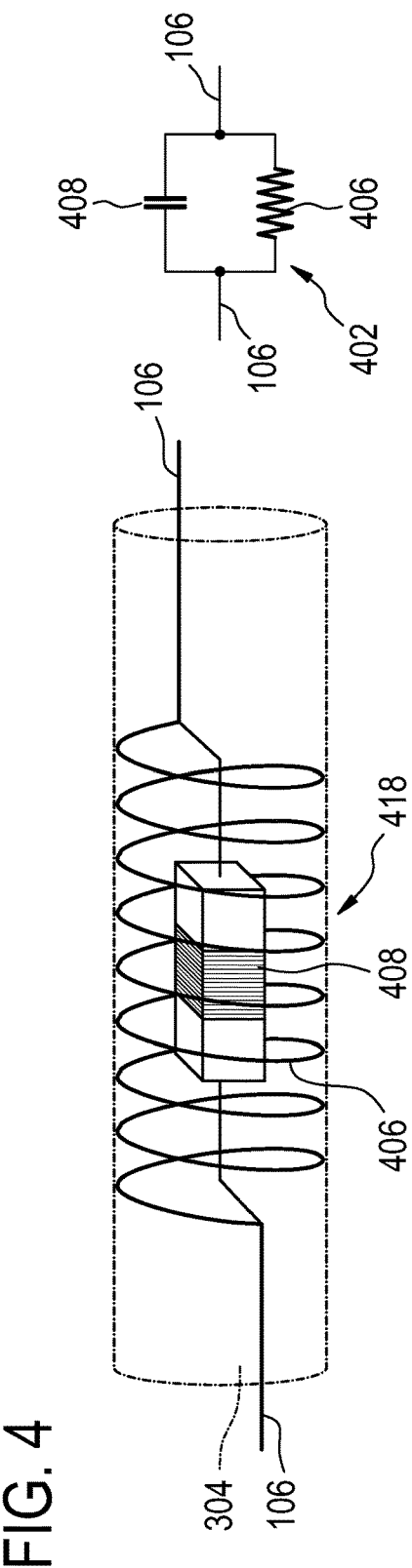

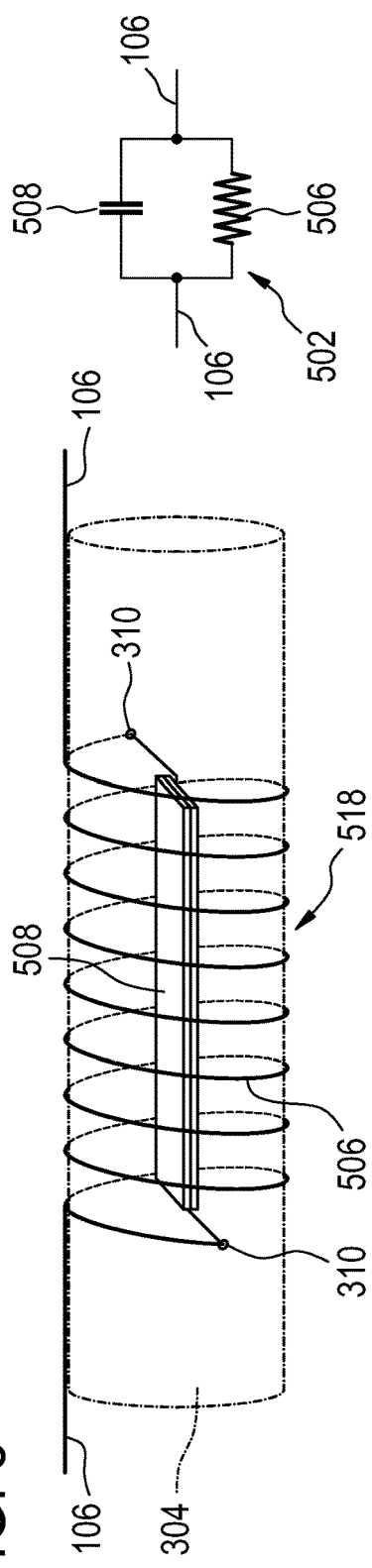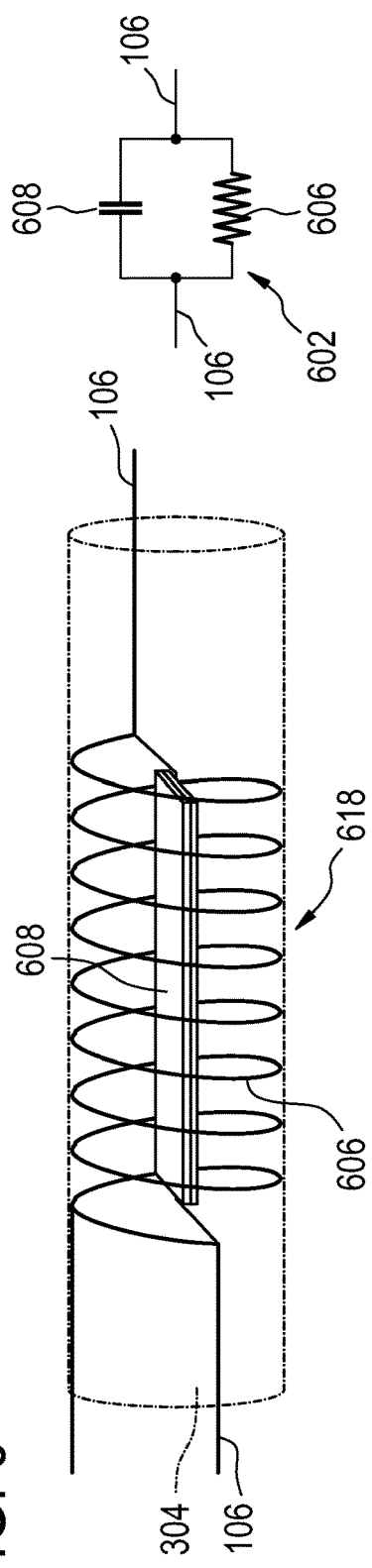
FIG. 5
FIG. 6

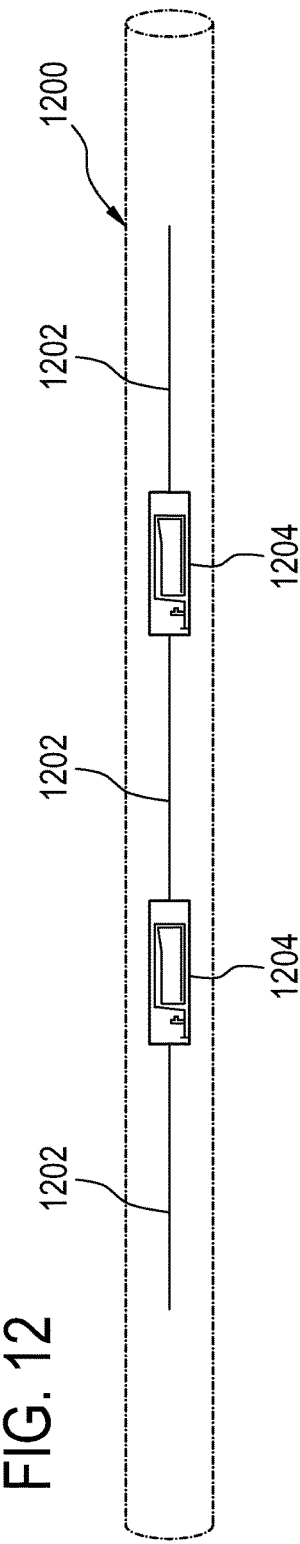

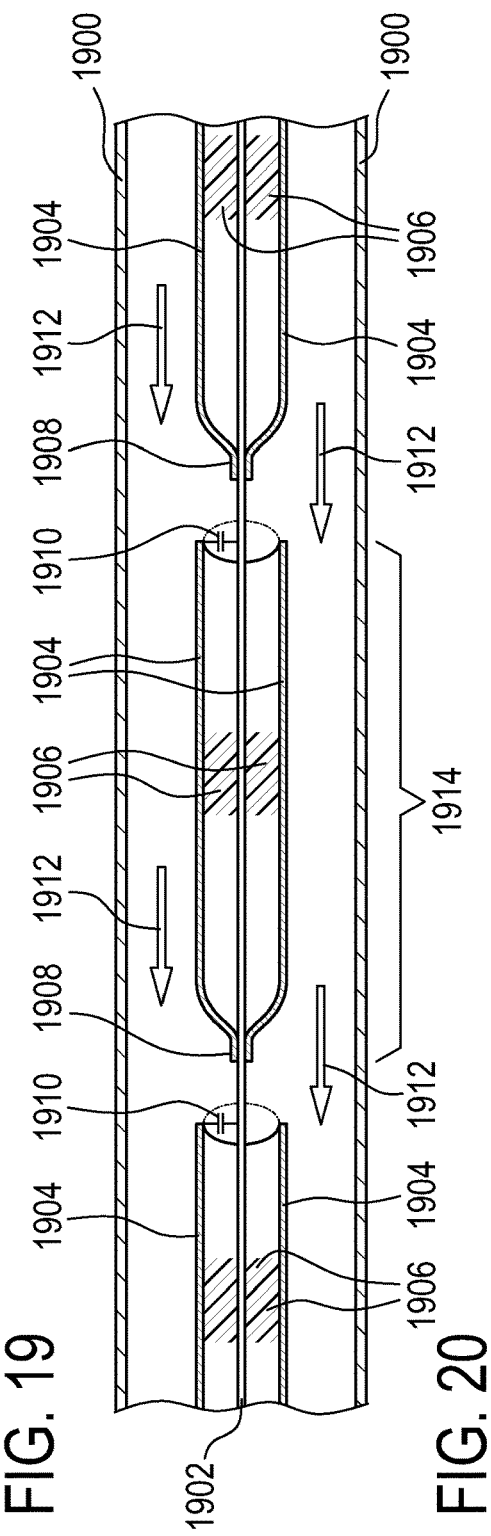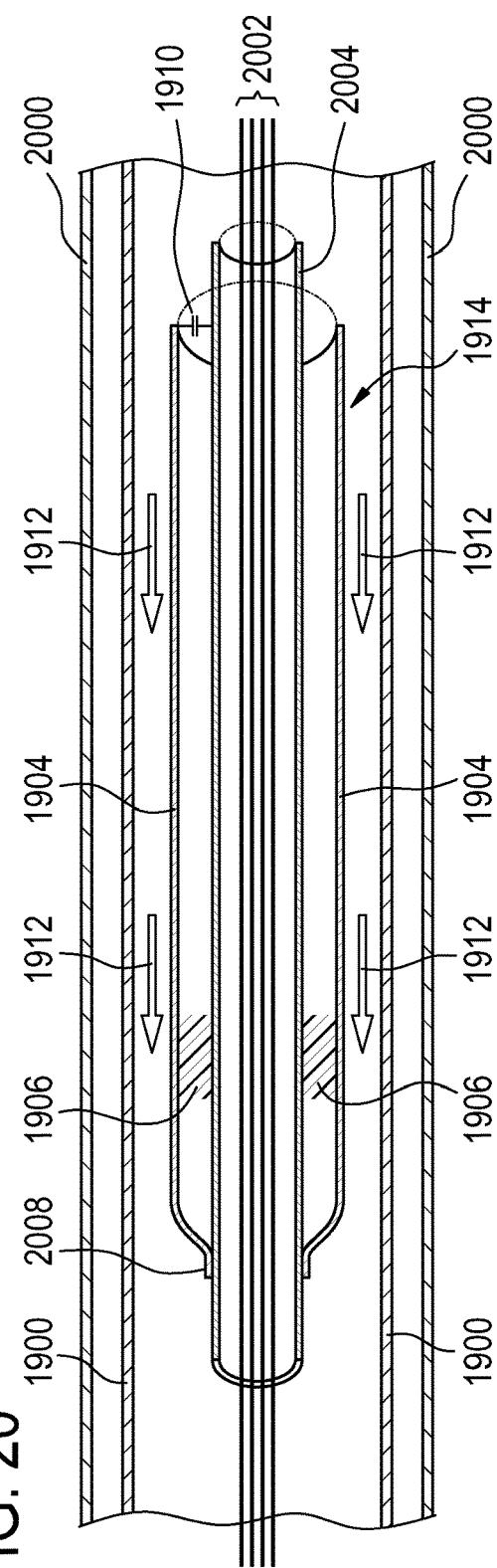

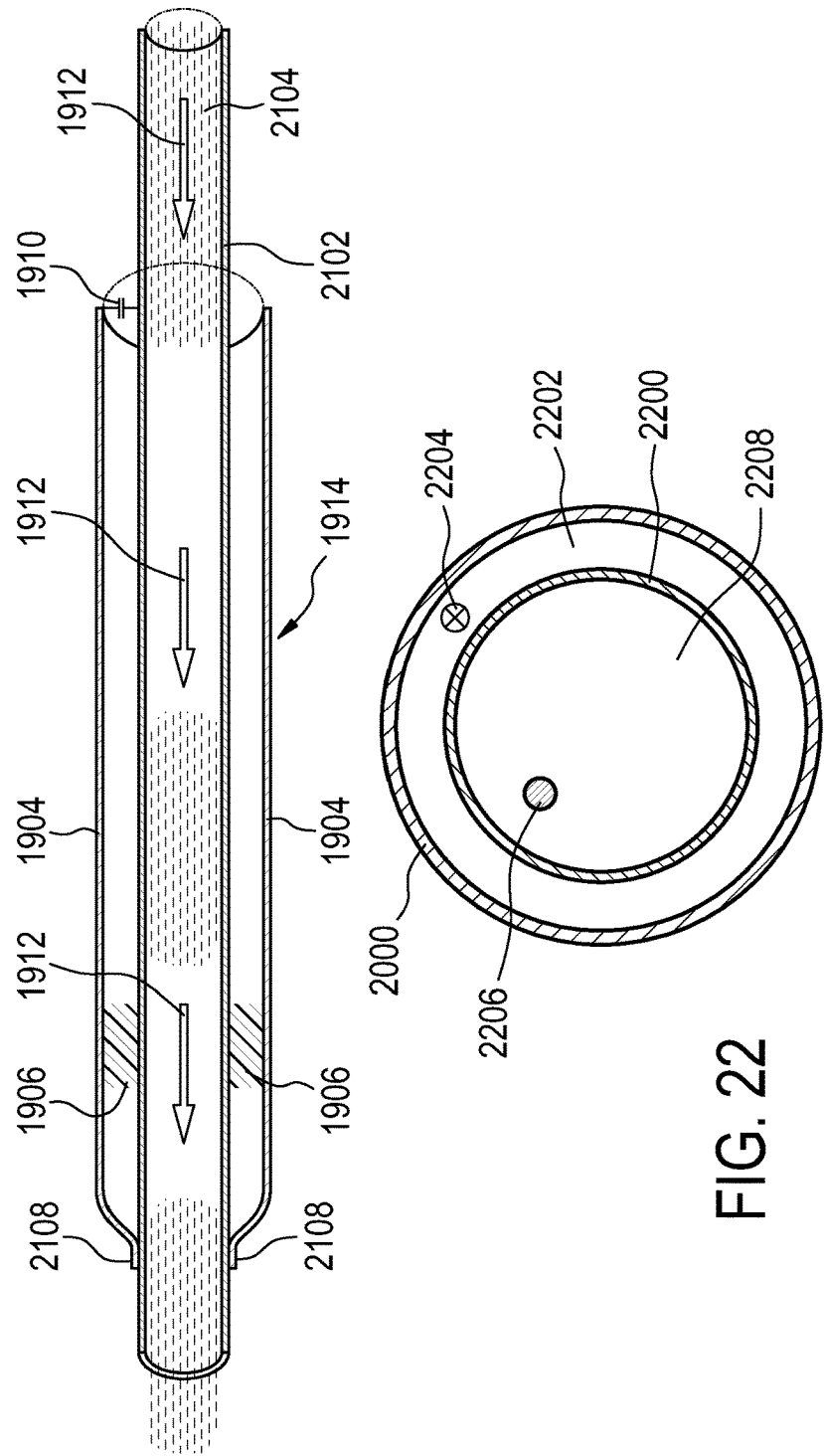

RADIO FREQUENCY ABLATION CATHETER AND MAGNETIC RESONANCE IMAGING SYSTEM

This application is a national stage application under 35 U.S.C. § 371 of international Application No. PCT/IB2010/054816 filed on Oct. 25, 2010 and published in the English language on May 5, 2011 as International Publication No. WO/2011/051872, which claims priority to European Application No. 09174740.2 filed on Nov. 2, 2009, the entire disclosures of which are incorporated herein by reference.

TECHNICAL FIELD

The invention relates to a catheter, in particular to catheters for use in magnetic resonance imaging systems.

BACKGROUND OF THE INVENTION

Radio frequency ablation catheters are used to ablate or destroy tissues by the use of electrical energy. A radio frequency ablation catheter may be inserted into a vein or artery. The use of X-ray based medical imaging techniques is known for guiding the placement and operation of radio frequency ablation catheters. Radio frequency ablation catheters have been successful in ablating heart tissue that causes rhythm disturbances and for the ablation of tissue in other therapies.

Modern conventional EP ablation catheters for use with X-ray imaging systems are equipped with tip cooling, mainly to avoid overheating and charring of tissue next to the tip, to avoid blood coagulation, and in consequence to allow for more RF power for deeper and faster ablation.

U.S. Pat. No. 7,388,378 discloses a device for protecting the conductive parts of an electrical device from current and voltage surges induced by the oscillating magnetic fields of a magnetic resonance imaging system.

SUMMARY OF THE INVENTION

The invention provides for a catheter and a magnetic resonance imaging system in the independent claims. Embodiments are given in the dependent claims.

X-ray imaging techniques are compatible with catheters that contain wires or transmission lines as X-rays do not induce currents on transmission lines. However, the attenuation of X-rays by hard structures in the body such as bone is larger than in soft tissues. This is a disadvantage of using X-ray imaging equipment for guiding a catheter, because for some uses, such as guiding a radio frequency ablation catheter for ablating soft tissues, imaging soft tissues is useful. In contrast, magnetic resonance imaging is able to effectively image soft tissues. Therefore, it would be advantageous to have a catheter such as a radio frequency ablation catheter that is compatible with magnetic resonance imaging. A difficulty of using magnetic resonance imaging to guide the use of a radio frequency ablation catheter is that the electromagnetic fields generated during the operation of a magnetic resonance imaging system may induce currents in the radio frequency transmission line used to deliver radio frequency power to the tip electrode of a radio frequency ablation catheter. Radio frequency ablation catheters may have a tip electrode, multiple electrodes, or distributed electrodes. It is understood herein that references to tip electrodes or electrodes apply equally to all electrodes of radio frequency ablation catheters.

Embodiment of the invention may provide a solution to this problem by using radio frequency traps that are distributed along a transmission line. It is understood herein that references and limitations to radio frequency transmission lines also apply to transmission lines. Radio frequency transmission lines are defined herein as transmission lines adapted for transmitting an electrical signal or electrical power at radio frequencies. A transmission line is defined herein as a wire or conductor adapted for transmitting an electrical signal or electrical power. Radio frequency traps suppress induced radio frequency currents and associated tip heating but may heat up themselves. For a radio frequency ablation catheter, the radio frequency traps may be cooled by a liquid that is provided to cool the electrode of the catheter. For this purpose, the traps may be designed such that locations of high electric fields of the trap that may cause radio frequency heating of adjacent lossy dielectrics are mostly confined to within or regions close to the cooling liquid. Heat transfer to the cooling liquid is optimized, while electric fields entering adjacent tissue of a subject are avoided. Hence, direct radio frequency heating of tissue adjacent to the catheter tube is excluded. Similarly, the inductive parts of the radio frequency trap that may be subjected to resistive heating are designed such that heat transfer to the cooling line is optimized and heat transfer to the body tissue is minimized. Hence, generation of excess heat in or near the radio frequency trap is minimized, and residual generated heat is constantly cooled so that the steady-state trap temperature is kept low which prevents radio frequency trap malfunction and secondary tissue heating.

The invention provides for a catheter comprising a transmission line. The transmission line comprises a plurality of radio frequency traps. The catheter further comprises a cooling line for cooling the plurality of radio frequency traps with a fluid. When catheters are used in an environment which has ambient radio frequency energy such as in a magnetic resonance imaging unit the transmission line may be able to pick up and have induced current on it due to the ambient radio frequency energy. Radio frequency traps may be used to prevent an induced current on the transmission line however the radio frequency energy is concentrated in the radio frequency traps which is eventually converted into heat. The fluid transported by the cooling line is used to distribute or remove heat from the radio frequency traps. This combination leads to a catheter which is safer for use in a magnetic resonance imaging system.

The entire transmission line may be cooled by the fluid in the cooling line or only a portion of the transmission line may be cooled. This depends upon the design of the radio frequency trap. The portion of the radio frequency trap that dissipates the radio frequency energy will be heated, and this is the portion of the radio frequency trap which is preferably cooled. For instance if discrete capacitors and inductors are used to form the radio frequency trap, then it is advantageous to have the discrete capacitors or inductors within the cooling line or in proximity to the cooling line so that heat can be removed by the cooling line.

There are many possible types of catheters which may be implemented as embodiments of the invention:
  Diagnostic EP catheters having several wires to connect the electrodes
  Actively tracked catheters having one or more wired miniature receive coils for localization in magnetic resonance procedures:
  angioplasty catheters for dilation of occluded vessels with or with out stent deployment valve replacement catheters
catheters for deployment of occluder devices for patent foramen ovale
Intravascular MR imaging catheters with wired internal MR imaging coils
Catheters that require wired sensors for physiological measurements:
pressure catheters for measurement of internal blood pressure
catheters for measurement of internal blood flow
catheters for measurement of internal blood temperature In another embodiment the catheter is a radio frequency ablation catheter. The transmission line is a radio frequency transmission line. The catheter further comprises an electrode. The cooling line is adapted for transporting the fluid to the electrode. The transmission line comprises a connection end and an electrode end. The connection end is adapted to be connected to a radio frequency generator. The electrode end is connected to the electrode. This embodiment is advantageous because it allows the radio frequency ablation catheter to be used in a high radio frequency field without interfering in the operation of the catheter. For instance radio frequency energy of hundreds of kilohertz may be used for ablating tissue in the vicinity of the electrode. The radio frequency traps may be constructed such that they block a different frequency of radio frequency energy. For instance the radio frequency field generated by a magnetic resonance imaging system could be blocked and prevented from causing an induced current on the transmission line which causes additional heating to the electrode.

In another embodiment the plurality of radio frequency traps comprises coaxial chokes. In this embodiment the transmission line is a coaxial cable. The outer shielding of the coaxial cable is cut at regular intervals. One end of the shielding is connected to the inner conductor of the coaxial cable and the other end is open or is optionally connected with a capacitor. The sections of the outer conductor of the coaxial cable are shorter than a quarter wavelength of a frequency which is desired to be blocked or trapped. Being shorter than a quarter wavelength prevents induced currents from building up on the outer conductor of the coaxial cable. This prevents an induced current from building up on the inner conductor of the coaxial cable.

A coaxial choke is also known as a coaxial trap and is commonly called a "bazooka balun." A coaxial choke creates a high impedance for currents flowing on the outside of a coaxial cable. Its original use was to suppress unbalanced currents at feed points of balanced antennas connected to an (unbalanced) coaxial cable ("balun"=balanced-unbalanced). The high impedance for external shield currents occurs at a basic frequency, according to the full wavelength. For magnetic resonance imaging, this is chosen to be the Larmour frequency, suppressing shield currents induced during a magnetic resonance radio frequency transmission.

In another embodiment, the transmission line comprises an outer shield electrode. The outer shield electrode comprises a plurality of sections that are spaced apart a maximum of a predetermined distance along the transmission line. The plurality of sections is connected electrically by the plurality of radio frequency traps. In an implementation of this embodiment, the outer shield could be the braided shield of a coaxial cable. The braided shield could be cut in to create electrically isolated sections. These electrically isolated sections could then be connected together electrically using the radio frequency traps. For instance a capacitor and an inductor in parallel could be used to connect two adjacent sections of the outer shield. This embodiment could use a single conductor or wire that is shielded by the outer shield from ambient radio frequency energy. Alternatively, multiple conductors or wires could be shielded by the outer shield. The radio frequency traps could be cooled by placing the transmission line within the cooling line, or by placing the components of the radio frequency trap in thermal contact with the cooling line.

In another embodiment the plurality of radio frequency traps each comprise a capacitor and an inductor connected in parallel. The radio frequency traps are spaced apart a maximum of a predetermined distance along the radio frequency transmission line.

In another embodiment the plurality of radio frequency traps comprises a printed circuit board. The inductor is formed on the printed circuit board. A coil of wire may be patterned on the printed circuit board. The inductor may be formed on a single layer of a circuit board or it may be formed on multiple layers.

In another embodiment the radio transmission line is formed on a printed circuit board. The inductor is formed on the printed circuit board. In this embodiment the entire or a substantial length of the transmission line of the catheter is made on a long narrow printed circuit board.

The invention provides for a catheter. The catheter may be a radio frequency ablation catheter. It is understood herein that references to radio frequency ablation catheters apply equally to other catheters which contain wires or transmission lines. An exception to this is that not all catheters which are embodiments of the invention comprise an electrode or tip electrode. The radio frequency ablation catheter comprises an electrode. The electrode may be a tip electrode. The electrode may be at any position along the position of the radio frequency ablation catheter. The radio frequency ablation catheter may also have multiple electrodes. All references to a tip electrode are understood to be applicable herein to any other electrodes which may be a component of a radio frequency ablation catheter. The radio frequency ablation catheter further comprises a cooling line adapted for transporting a fluid to the tip electrode. The radio frequency ablation catheter further comprises a radio frequency transmission line. The radio frequency transmission line comprises a connection end and an electrode end. The connection end is adapted to be connected to a radio frequency generator. The electrode end is connected to the tip electrode. The radio frequency transmission line comprises a plurality of radio frequency traps. The plurality of radio frequency traps each comprises a capacitor and an inductor connected in parallel. The radio frequency traps are spaced apart a maximum of a predetermined distance along the radio frequency transmission line. The cooling line is adapted for cooling the plurality of radio frequency traps.

The radio frequency traps are tuned to blocking frequency. When the radio frequency ablation catheter is used in a magnetic resoancance imaging system it is desirable to tune the radio frequency traps to the Larmour frequency of the magnetic resoance imaging system by choosing inductance L and capacitance C such that $$\omega = \frac{1}{\sqrt{LC}},$$

where ω is the Larmour frequency. Coil and distributed capacitors are additionally constrained by the dimensions of cooling line.

Coil design (number of windings, winding density) and choice of capacitance may be determined by mounting test coils onto the cooling tube and/or by choice of an appropriate lumped or distributed capacitors. The resonance frequency of the resulting trap may be measured as follows: The port of a network analyzer is connected to a circular pick-up coil that is used to couple weakly inductively to the coil L. The S11 mode of the network analyzer then shows a minimum of reflected power at the resonance frequency of the RF trap.

Iteratively, coil parameters and capacitors may be varied to adjust the resonance frequency to ω.

Fine tuning of the radio frequency trap in the fully assembled state may be achieved by changing the winding density of the coil. For this purpose, the coil should be wound loosely onto the cooling tube during assembly, and only after measurement of the resonance frequency of the RF trap and fine tuning by slight variation of the winding positions, the coil windings may be fixed by an adhesive.

When the radio frequency ablation catheter is connected to a radio frequency generator, radio frequency electrical power is transmitted to the tip electrode via the radio frequency transmission line. The radio frequency electrical power from the radio frequency generator heats the tissue next to the tip electrode due to the local high current density which causes local ablation of tissue. Tissue which is not adjacent to the tip electrode is heated by the conduction of heat from the region of tissue that is heated. The cooling line transports a fluid to the tip electrode to prevent the tissue directly adjacent to the tip electrode from becoming too hot. Several different varieties may be used. For instance the cooling line may carry a saline solution to the tip which then leaks cooling fluid into tissue adjacent to the tip electrode for the purpose of tip irrigation. Alternatively, a closed loop can be used where preferably a first tube transports a cooling fluid into the tip for the purpose of cooling of the tip, and the cooling line equipped with traps is used to provide the return path for the cooling liquid. Alternatively, the traps may be cooled by the first tube. In all closed loop set-ups no liquid leaks into the body, which allows use of cooling liquids other than saline.

The radio frequency traps may comprise a capacitor and inductor that are connected in parallel. This allows the frequency trap to be tuned to a narrow frequency band. Essentially the capacitor and inductor form a notch filter. Placing the radio frequency traps along the length of the radio frequency transmission line periodically allows the radio frequency ablation catheter to be used in a region with a varying radio frequency electromagnetic field. The radio frequency traps can be tuned so that they have a high impedance at the resonance frequency of the radio frequency trap and prevent the radio frequency electromagnetic field from inducing a current on the radio frequency transmission line. The radio frequency traps block this current by storing energy within the capacitor and inductor. This stored energy is eventually converted into heat and this is why the cooling line is used for cooling the radio frequency traps. The cooling tube cools both the tip electrode and the radio frequency traps.

In another embodiment the capacitor is within the cooling line. This embodiment is beneficial because the capacitor is surrounded by coolant and also the capacitor is within the cooling line and further from the catheter wall. The catheter wall is a tube or housing which surrounds the cooling line and the radio frequency transmission line.

In another embodiment the cooling line has an exterior surface. The capacitor is in contact with the exterior surface. The capacitors which make up the traps are placed in contact with the cooling line in order to transfer heat away from them.

In another embodiment the inductor comprises a coil. The coil is within the cooling line. The coil of each of the plurality of radio frequency traps is placed within the cooling line. This is advantageous because the fluid which is used to cool the tip electrode is able to cool each of the coils which make up the plurality of radio frequency traps.

In another embodiment the cooling line has an exterior surface. The inductor comprises a coil. The coil is wrapped around the exterior surface. This embodiment is advantageous because the coil is placed in contact with the cooling line and can be used to efficiently cool the coil. In this way the coils which make up the inductors for each of the plurality of radio frequency traps is cooled.

In another embodiment the capacitor is a lumped capacitor. A lumped capacitor as used herein is a capacitor where the electrodes and the dielectric layer used to form the capacitor are folded. Capacitors that are used as electrical components for electrical devices are typically lumped capacitors.

In another embodiment the capacitor is a distributed capacitor. A distributed capacitor as used herein is a capacitor whose electrodes and dielectric layer are not folded. An example of a distributed capacitor would be two flat electrodes with a dielectric layer between the two.

In another embodiment the capacitor comprises a dielectric layer. The cooling line forms the dielectric layer. For instance the cooling line may comprise a dielectric layer. An electrode could be placed on the interior and exterior of the cooling line opposing each other. This would then form a capacitor.

In another embodiment the capacitor comprises a first electrode. The capacitor further comprises a dielectric layer. The capacitor further comprises a second electrode. The dielectric layer is in contact with the first electrode and the second electrode. The surface area of the first electrode is larger than the surface area of the second electrode. The second electrode is in contact with the cooling line. The plurality of radio frequency traps function by storing energy within the capacitor and the inductor. As a result there can be large electric fields between the first electrode and the second electrode. By having the second electrode smaller than the first electrode and having the second electrode in contact with the cooling line the large electric fields are directed away from the catheter wall. This has the benefit that when the radio frequency ablation catheter is used within a subject, the large electric fields of the capacitors will not cause heating in the subject.

In another embodiment the first electrode and the second electrode have a curvature that matches the curvature of the cooling line. This embodiment is advantageous because the second electrode is smaller than the first electrode and is in contact with the cooling line. The curved surface further directs the large electric fields to the interior of the cooling line. This further reduces the large electric field of the plurality of radio frequency traps.

In another embodiment the radio frequency line comprises a conductive tube. The conductive tube may cover the surface of the cooling line or the conductive tube and the cooling line may be the same component. If they are separate components then the cooling line may be a dielectric tube. The radio frequency trap comprises a gap in the conductive tube. If the conductive tube and the cooling line are the same component, then the conductive tube will cover the surface of a dielectric tube. The inductor is connected across the gap in the conductive tube and may be wrapped around the dielectric tube. The capacitor comprises a third electrode. The capacitor further comprises the conductive tube. The third electrode is mounted inside the dielectric tube. The radio frequency line is the conductive tube. The inductor may be formed by a coil of wire wrapped either inside or outside of the dielectric tube across the gap. If the coil is on the inside of the dielectric tube then the coil may needs to go through or around the dielectric tube in order to contact the conductive tube. The third electrode may be implemented in several different ways also. The third electrode could comprise two separate sub-electrodes which are located inside the cooling line. The sub-electrodes would each form a capacitor with the conductive tube on either side of the gap in the conductive tube. The two sub-electrodes could then be electrically connected together. If a separate cooling line and conductive tube are used, there would be no need to make a hole to form the capacitor. Alternatively there could be an electrical connection which goes through the cooling line and attaches to one end of the conductive tube. There would then be a wire which is connected to the third electrode and then the third electrode is connected to the inside of the conductive tube.

In another embodiment the tip electrode comprises a temperature sensor. This embodiment is particularly advantageous, because the temperature sensor can be used to monitor the temperature of the tip electrode when the radio frequency ablation catheter is in use. If the tip electrode heats more than is expected then this may be an indication that one or more of the radio frequency traps has failed. This is because if the radio frequency traps fail then a current could be induced in the radio frequency transmission line.

In another aspect the invention provides for a magnetic resonance imaging system. The magnetic resonance imaging system comprises a magnet adapted for generating a magnetic field for orienting magnetic spins of nuclei of a subject located within the imaging volume. The magnetic resonance imaging system further comprises a radio frequency system for acquiring magnetic resonance data. Magnetic resonance data as defined herein as the representation of radio signals acquired during the process of operating a magnetic resonance imaging system. For instance during the operation of a magnetic resonance imaging system gradient fields and radio frequency fields are used to manipulate and control the orientation of magnetic spins of nuclei. When the magnetic spins relax they emit radio frequencies which can be detected using an antenna and recorded. The recording of these radio transmissions from the magnetic spins is the magnetic resonance data. Magnetic resonance data can be transformed using Fourier techniques into images or visualizations of the imaging volume of the subject. The radio frequency system comprises a radio frequency transceiver and a radio frequency coil. It is understood that the radio frequency transceiver could in fact be a separate transmitter and a separate receiver. The radio frequency coil could also be a separate transmit coil and a separate receive coil. The magnetic resonance imaging system further comprises a magnetic field gradient coil for spatial encoding of the magnetic spins of the nuclei within the imaging volume. The magnetic resonance imaging system further comprises a magnetic field gradient coil power supply for supplying current to the magnetic field gradient coil. The magnetic resonance imaging system further comprises a subject electrode adapted for forming an electrical connection with the subject. The magnetic resonance imaging system further comprises a subject support adapted for receiving the subject. The subject electrode may be integrated into the subject support.

The magnetic resonance imaging system further comprises a radio frequency generator for producing radio frequency power at a first frequency. The radio frequency generator is connected to the subject electrode. The radio frequency generator is adapted for connecting to a radio frequency ablation catheter according to an embodiment of the invention. When the radio frequency ablation catheter is placed within a subject that is in contact with the subject electrode, a complete electrical circuit is formed through the catheter, the subject and then back through the subject electrode. The magnetic resonance imaging system further comprises a computer system adapted for constructing images from the magnetic resonance data and for controlling the operation of the magnetic resonance imaging system. The computer system is adapted for generating magnetic resonance images of the subject when the radio frequency generator is operational. This magnetic resonance imaging system is beneficial, because the magnetic resonance images can be used to guide the use of the radio frequency ablation catheter by a physician or operator.

In another embodiment the radio frequency generator is adapted for generating radio frequency power at a test frequency. The test frequency would be preferentially a frequency to which the plurality of radio frequency traps is tuned to. The radio frequency generator is adapted for generating the test frequency at lower power than the first frequency. The radio frequency generator comprises a reflected power meter for measurement the reflected power of the test frequency. The radio frequency generator is adapted for detecting a malfunction of at least one of the plurality of radio frequency traps using the reflected power. The radio frequency generator is further adapted for signaling the computer system when the malfunction is detected. One way of measuring the power is by incorporating a network analyzer functionality into the radio frequency generator. Alternatively, the reflected power meter may function by measuring the standing wave ratio at the test frequency.

The computer system is further adapted for reducing the generation of radio frequency power by the radio frequency transceiver when the computer system is signaled by the radio frequency generator. The generation of radio frequency power may be also stopped when the computer system is signaled by the radio frequency generator. In this embodiment the test frequency is used to test if the radio frequency traps are functioning. If a trap becomes shorted or open then the impedance at the test frequency may change. As was mentioned before the test frequency could be at the frequency for which the radio frequency traps are tuned. Alternatively the test frequency could also be at a different frequency, for instance a frequency that is higher than the test frequency and the first frequency or at a frequency which is intermediate to the first frequency and the Larmour frequency of a hydrogen atom in the magnet of the magnetic resonance imaging system. If a radio frequency trap fails the impedance and therefore the reflected or transmitted power of the test frequency may change. It is understood herein that a measurement of the reflected power is equivalent to a measurement of the transmitted power at the test frequency. This may indicate a failed radio frequency trap.

In another embodiment the radio frequency ablation catheter has a tip electrode which comprises a temperature sensor. The radio frequency generator is further adapted for determining a temperature measurement of the tip electrode using the temperature sensor. The computer system is further adapted for receiving the temperature measurement from the radio frequency generator. The computer system is further adapted for reducing the generation of radio frequency power by the radio frequency transceiver when the temperature measurement is above a predetermined safety threshold. If the plurality of radio frequency traps has a trap which fails, this may induce a current in the radio frequency transmission line. This may lead to a heating of the tip electrode. By monitoring the temperature of the tip electrode for an abnormal increase in temperature during operation may allow the detection of failed radio frequency traps.

In another embodiment, the catheter may comprise sensors to measure the temperature of the cooling liquid. An elevated temperature of the cooling may also be used for detecting the malfunction of a radio frequency trap or otherwise strong radio frequency coupling of the magnetic resonance system to the catheter e.g. also due to incorrect use of the magnetic resonance imaging system or the catheter.

Moreover, the temperature measured at the tip of the catheter, e.g. the measured temperature of the cooling liquid, can be employed to control various RF functions of the magnetic resonance examination system. In particular the radio frequency power delivered by the radio frequency ablation catheter can be accurately regulated on the basis of the temperature measured at the tip of the catheter. In another aspect, the power level of the RF excitation field of the magnetic resonance examination system can be controlled on the basis of the temperature measured at the tip of the catheter. Thus, the SAR level deposited in/on the patient' body is controlled on the basis of temperature measured at the tip of the catheter. This control of the RF functions of the magnetic resonance examination system on the basis of the temperature measured at the tip of the catheter can be advantageously employed independently of the monitoring of failure of switchable traps in the transmission line.

BRIEF DESCRIPTION OF THE DRAWINGS

In the following preferred embodiments of the invention will be described, by way of example only, and with reference to the drawings in which:

FIG. 1 illustrates an embodiment of a radio frequency ablation catheter according to an embodiment of the invention;

FIG. 2 illustrates a further embodiment of a radio frequency ablation catheter 200 according to an embodiment of the invention;

FIG. 3 illustrates a section of cooling line with an embodiment of a radio frequency trap according to the invention;

FIG. 4 illustrates a section of cooling line with a further embodiment of a radio frequency trap according to the invention;

FIG. 5 illustrates a section of cooling line with a further embodiment of a radio frequency trap according to the invention;

FIG. 6 illustrates a section of cooling line with a further embodiment of a radio frequency trap according to the invention;

FIG. 12 shows a section of cooling line of a catheter according to an embodiment of the invention;

FIG. 13 shows an embodiment according to the invention of a transmission line manufactured using a printed circuit board;

FIG. 19 shows a section of cooling line according to an embodiment of the invention with a transmission line that has coaxial chokes;

FIG. 20 shows a section of a catheter according to an embodiment of the invention with a transmission line 1902 that has coaxial chokes;

FIG. 21 shows a further embodiment according to an invention of a cooling line with a coaxial choke;

FIG. 22 shows a further embodiment according to the invention of a catheter.

DETAILED DESCRIPTION OF THE EMBODIMENTS

Figure 7:
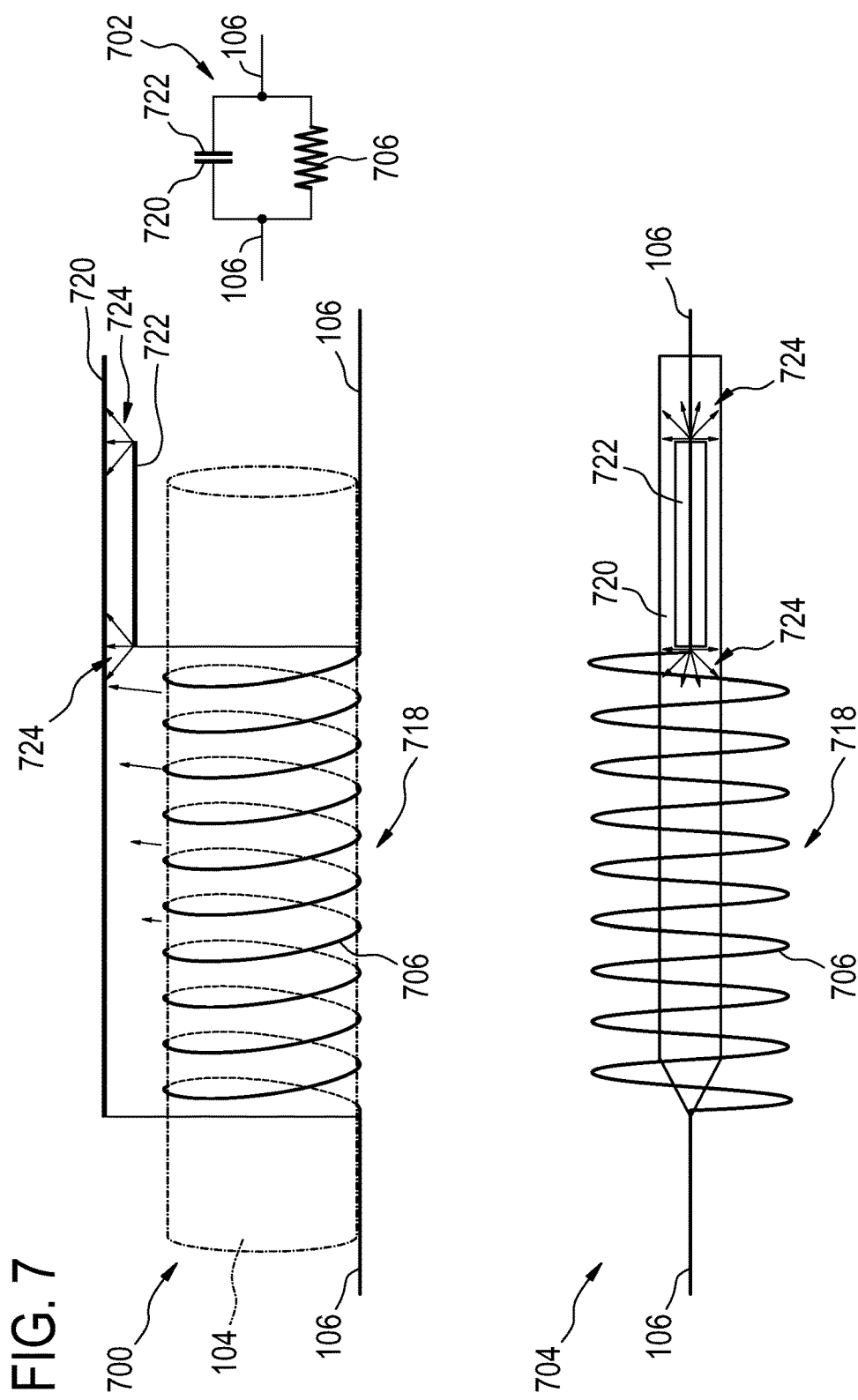
FIG. 7 illustrates a section of cooling line with a further embodiment of a radio frequency trap according to the invention.

Like numbered elements in these figures are either equivalent elements or perform the same function. Elements which have been discussed previously will not necessarily be discussed in later figures if the function is equivalent.

FIG. 1 illustrates an embodiment of a radio frequency ablation catheter 100 according to an embodiment of the invention. The radio frequency ablation catheter 100 has a catheter wall 102. Within the catheter wall 102 is a cooling line 104. The catheter wall 102 may be a tube. The catheter wall 102 is typically 2 mm to 3 mm in diameter. At the end of the catheter wall 102 is a tip electrode. In the embodiment shown in FIG. 1 there is a radio frequency transmission line 106 which is shown running through the cooling line 104. The radio frequency transmission line 106 has an electrode end 108 which is connected to the tip electrode 110. The tip electrode 110 is at the end of the catheter wall 102. The arrow labeled 112 shows the direction of fluid which is used to cool the tip electrode 110. In this embodiment the tip electrode 110 has a channel 114 or channels in the tip electrode which allow fluid to exit the tip electrode 110. The arrows labeled 116 indicate the flow of fluid out of the tip electrode channel 114. In typical use one liter per hour of fluid, which is typically a saline solution, is used. The radio frequency transmission line 106 also comprises radio frequency traps 118. The radio frequency traps 118 are shown as being spaced a predetermined distance 120 apart. The radio frequency traps 118 are tuned to a particular blocking frequency. Radio frequency traps are constructed of an inductor and a capacitor in parallel. This produces a so called notch filter. Often the predetermined distance 120 is smaller than a wavelength of an electromagnetic wave at the blocking frequency in the medium to which the radio frequency ablation catheter is placed. For practical purposes a material which could be used to calculate the wavelength could be water because radio frequency ablation catheters are typically used within tissue which is comprised mostly of water. By placing these radio frequency traps 118 at a distance less than a wavelength this impedes the generation of a current on the radio frequency transmission line 106 by an external electromagnetic wave at the blocking frequency. It may be beneficial to place several radio frequency traps 118 within one wavelength. This is because if a single radio frequency trap fails then a current will still not be able to be induced on the radio frequency transmission line 106.

In the embodiment shown in FIG. 1 the radio frequency transmission line 106 and the radio frequency trap 118 are both shown as being within the cooling line 104. The radio frequency transmission line 106 may be inside or outside of the cooling line 104. The radio frequency trap 118 may also be inside or outside of the cooling line 104. If the radio frequency trap 118 is not within the cooling line 104, then the components which make up the radio frequency trap 118 are preferentially in contact with the cooling line 104.

FIG. 2 shows a further embodiment of a radio frequency ablation catheter 200 according to an embodiment of the invention. The design of the radio frequency ablation catheter 200 shown in FIG. 2 is very similar to the design of the radio frequency ablation catheter 100 shown in FIG. 1. The design of the tip electrode 210 and the method of cooling the tip electrode 210 differs from that as shown in FIG. 1. There is a tip electrode 210 which is connected to the cooling line 104 and radio frequency transmission line 106 as was shown in FIG. 1. The tip electrode 210 also has a channel 214 for the fluid which is used to cool the tip electrode 210. However in this embodiment the fluid does not exit the tip electrode 210 but returns back within the cavity 216 formed by the catheter wall 102. The arrow labeled 212 indicates the direction of fluid flow out of the channel of the tip electrode 214 and back through the cavity 216 formed by the catheter wall 102. The fluid flow out of the channel may also be through an additional line.

In this embodiment there is also a temperature sensor 202 within the tip electrode 210. The temperature sensor 202 may be used to monitor the temperature of the tip electrode 210 during operation. An abnormally high temperature of the tip electrode 210 during operation may indicate the failure of one or more radio frequency traps 118. There is a high impedance line 204 connecting to the sensor temperature 202. The temperature sensor 202 may be implemented using a temperature sensor such as a thermal couple. The high impedance line 204 may be wire connections which have a sufficiently high impedance that it is not necessary to provide an impedance to block the generation of current on the high impedance line 204. Alternatively, the temperature sensor 202 may be connected to the radio frequency transmission line 104. The read-out unit for signals of the temperature sensor 202 would then be equipped with an AC blocking circuit to reject the radio frequency electrical power used for ablation, but not the low frequency signals used for temperature sensing.

FIG. 3 illustrates a section of cooling line 304 with an embodiment of radio frequency trap 318 according to the invention. An equivalent circuit 302 is also shown. The components in the equivalent circuit 302 are labeled identically with those of the radio frequency trap 318. Exterior to the cooling line 304 is the radio frequency transmission line 106. A coil 306 wrapped around the cooling line 304 forms the inductor of the radio frequency trap 318. Within the cooling line 304 is a lumped capacitor 308. There are holes 310 in the cooling line to connect the lumped capacitor 308 to the radio frequency transmission line 106.

FIG. 4 illustrates a further embodiment of a radio frequency trap 418 that is similar to that shown in FIG. 3. FIG. 4 also has an equivalent circuit diagram 402 which labels components in the same way as is shown for the section of cooling line 304. There is a section of cooling line 304 shown. In this embodiment the radio frequency transmission line 106 is connected to a coil 406 which is located inside of the cooling line 304. Connected in parallel with the coil 406 is a lumped capacitor or capacitance 408. Both the coil 406 and the lumped capacitor 408 are located within the cooling line 304 in this embodiment.

FIG. 5 illustrates a further embodiment of a radio frequency trap 518. There is also an equivalent circuit 502 where the components are labeled. In this embodiment the cooling line 304 has the radio frequency transmission line 106 exterior to it. There is a coil 506 wrapped around the cooling line 304. Interior to the cooling line 304 is a distributed capacitor 508. The cooling line has holes 310 which allow electrical connection between the radio frequency transmission line 106 and the distributed capacitor 508. In this example the distributed capacitor 508 is shown as being two electrodes with a dielectric between them. The advantage of this embodiment is that the distributed capacitor 508 has a very large surface area. This aids in cooling the distributed capacitor 508.

FIG. 6 shows a further embodiment of a radio frequency trap 618. In this figure there is an equivalent circuit 602 which shows the components of the radio frequency trap 618. In this embodiment there is a cooling line 304. Interior to the cooling line is the radio frequency transmission line 106. There is a coil 606 and a distributed capacitor 608 which are both within the cooling line.

In the embodiments shown in FIG. 3 and FIG. 5, the capacitors (lumped or distributed) and all conductive parts causing local high electrical E-fields are fully immersed inside the cooling liquid. This fully excludes high field strength to enter the tissue of the patient. The constant flow through the cooling liquid tube effectively "blurs" the dangerous local specific absorption ration (SAR) hot spot by distributing the heat with the liquid convection or even removes the heat completely from the system in case of the closed-irrigation approach. FIG. 4 and FIG. 6 depict variants of the embodiments FIGS. 3 and 5. In these embodiments, the radio frequency transmission line 106 is routed inside the cooling tube, which further reduces the overall profile of the assembly. In all embodiments where parts of the radio frequency traps or the ablation cable are routed inside the cooling tube, preferably a biocompatible isolative coating is applied to such parts to achieve biocompatibility and to prevent leakage of radio frequency currents from such parts into the cooling liquid which would lead to minor parasitic radio frequency heating of the cooling liquid inside the cooling tube.

FIG. 7 shows a further embodiment of a radio frequency trap 718. There is a side view 700 shown, an equivalent circuit view 702 and a bottom view 704. The bottom view 704 does not show the cooling line 104. The radio frequency transmission line 106 is shown as being exterior to the cooling line 104. There is a coil 106 wrapped around the cooling line 104. There is a capacitor which is formed by a first electrode 720 and a second electrode 722. The first electrode 720 has a larger surface area than the second electrode 722. Additionally the second electrode 722 is adjacent to the cooling line 104. The first electrode 720 in this embodiment is used as a shield against electric field lines 724. The radio frequency trap 718 may store large amounts of electromagnetic energy. The use of the first electrode 720 as a shield improves the safety of the radio frequency trap 718. Alternatively the radio frequency transmission line 106 and/or the coil 706 and/or the first electrode 720 and/or second electrode 722 may be located within the cooling line 104.

Figure 8:
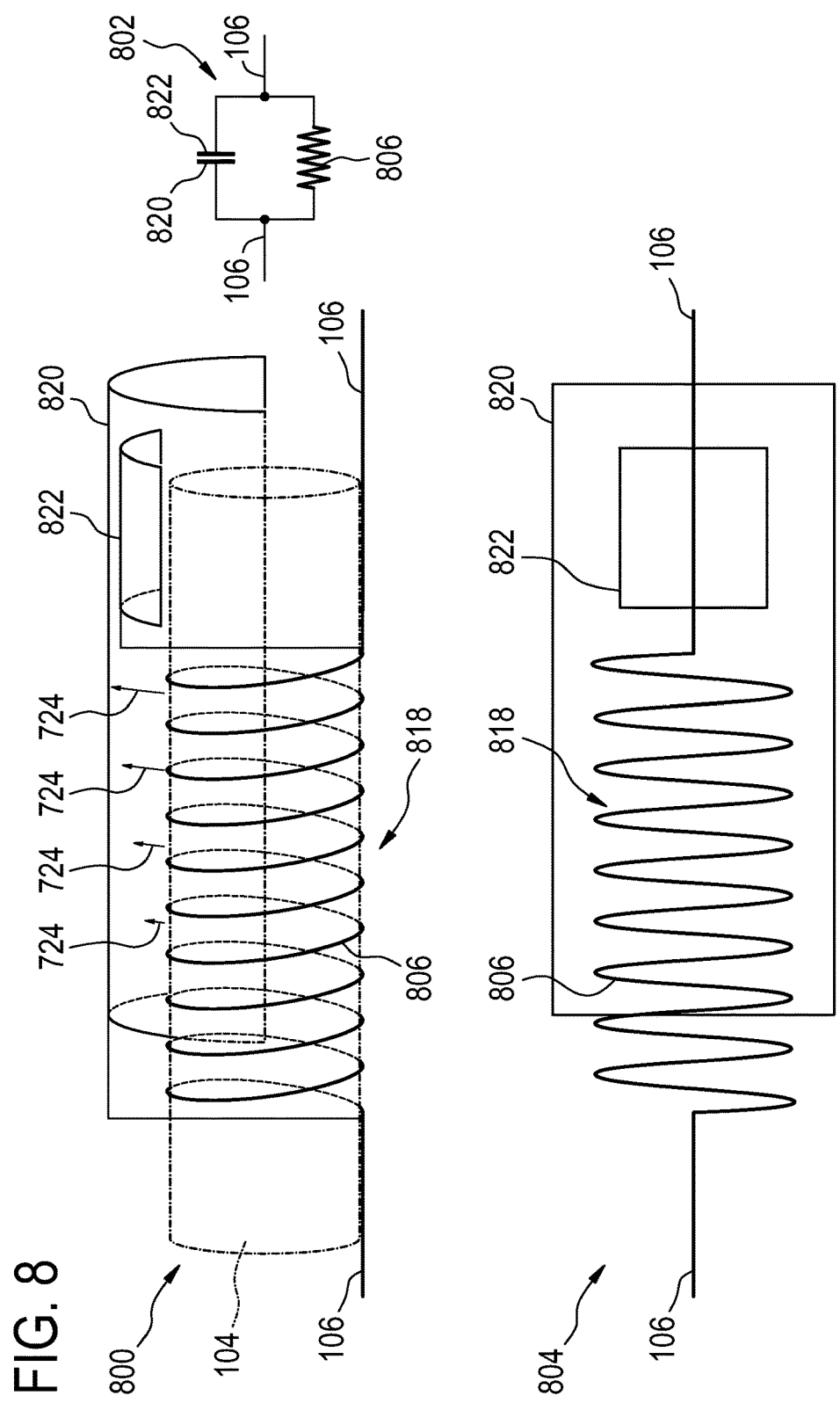
FIG. 8 illustrates a section of cooling line with a further embodiment of a radio frequency trap according to the invention.

FIG. 8 shows a similar embodiment to that shown in FIG. 7. In FIG. 8 a side view of a section of cooling line 104 with a radio frequency trap 118 is shown. View 802 shows an equivalent circuit with the components labeled. View 804 shows a bottom view of view 800 but without the cooling line 104 shown. Shown are radio frequency transmission lines 106 which are exterior to the cooling line 104. There is a coil 806 which is wrapped around the cooling line 104. Connected in parallel with the coil 806 is a capacitor which is formed by a first electrode 820 and a second electrode 822. In this embodiment the first electrode 820 and the second electrode 822 are shown as having a curvature which matches that of the cooling line 104. The actual curvatures shown in the fig. are exaggerated to make them more visible. As with the embodiment shown in FIG. 7 the radio frequency transmission line 106 and/or the coil 806 and/or the first electrode 820 and/or the second electrode 822 may be located inside of the cooling line 104.

Figure 9:
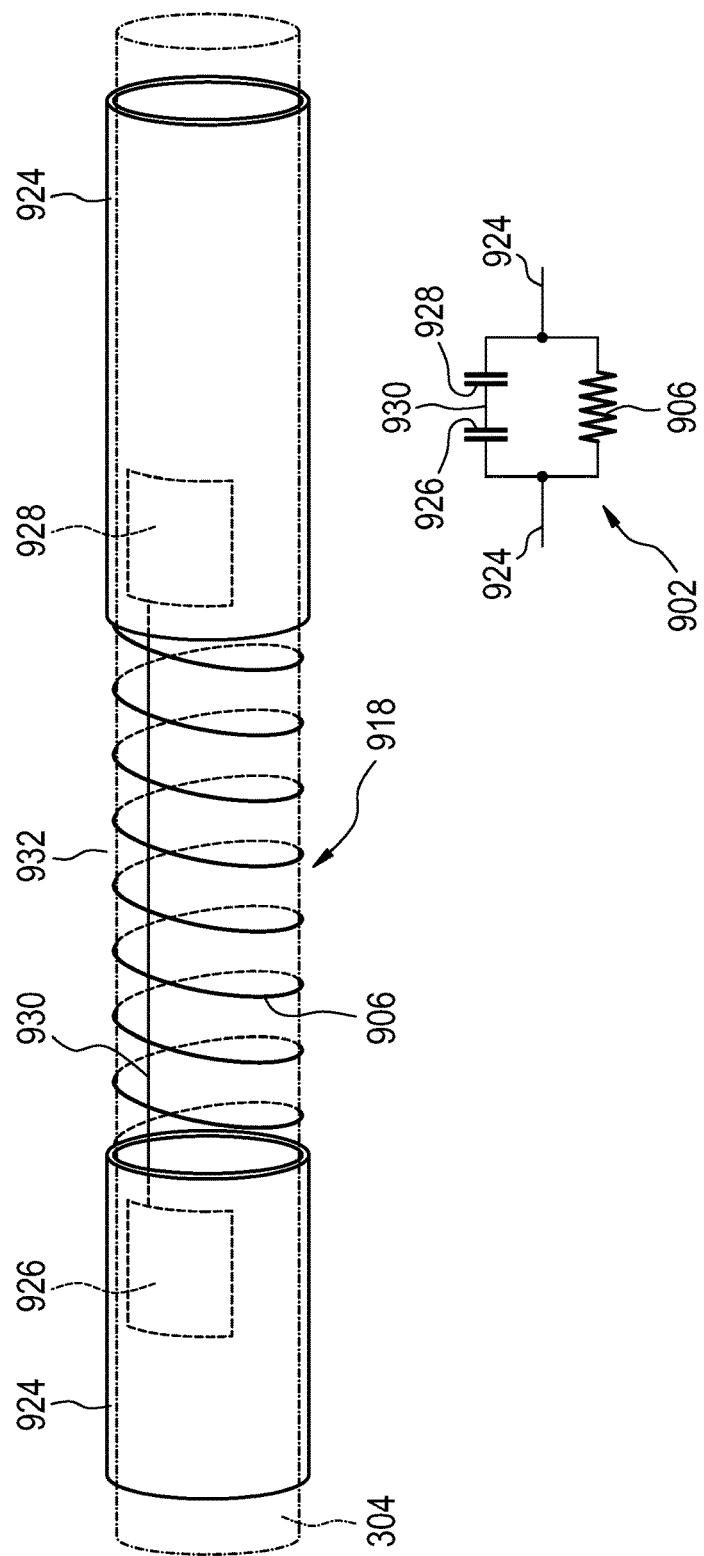
FIG. 9 illustrates a section of cooling line with a further embodiment of a radio frequency trap according to the invention.

FIG. 9 illustrates a radio frequency trap 918 according to an embodiment of the invention. The equivalent circuit 902 is also shown and components are also labeled in this equivalent circuit diagram 902. In FIG. 9 a cooling line 304 is shown. The cooling line 304 may comprise a dielectric. In this embodiment the radio frequency transmission line is a conductive tube 924. The radio frequency trap 918 is formed around a gap 932 in the conductive tube 924. Between the two sections of the conductive tube 924 is a coil 906 which forms the inductor of the radio frequency trap 918. The capacitor is formed by a third electrode 926 and a fourth electrode 928. These electrodes are mounted inside of the cooling line 304. The third electrode 926 and the fourth electrode 928 are mounted on opposite ends of the gap 932 in the conductive tube 924. The third electrode 926 and the fourth electrode 928 are capacitively coupled to a section of the conductive tube 924. The third electrode 926 and a fourth electrode 928 are connected by a wire 930 or some other conductor. The third electrode 926 and the fourth electrode 928 could also be mounted on the outside of the conductive tube 924. However it is advantageous to have the third electrode 926 and the fourth electrode 928 within the cooling line 304. This is because the conductive tube 924 shields any high electric fields which may be around the edges of the third electrode 926 or the fourth electrode 928.

Figure 10:
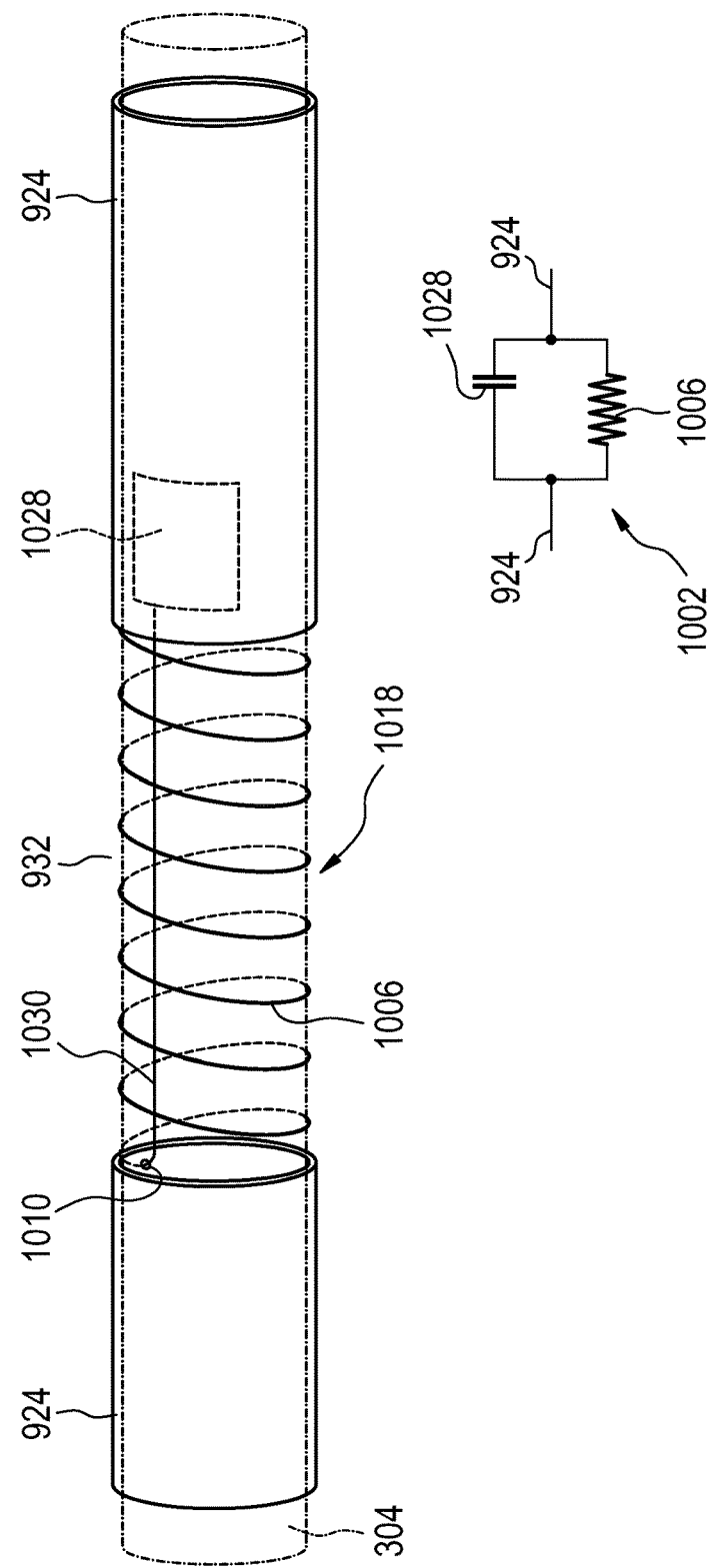
FIG. 10 illustrates a section of cooling line with a further embodiment of a radio frequency trap according to the invention.

FIG. 10 shows a similar embodiment to that shown in FIG. 9. FIG. 10 shows an embodiment of a radio frequency trap 918 according to an embodiment of the invention. Equivalent circuit 1002 is also shown. Components are also labeled on the equivalent circuit diagram 1002. In FIG. 10 a cooling line 304 is shown. The radio frequency transmission line is a conductive tube 924. As with the embodiment in FIG. 9, there is a gap 932 in the conductive tube 924 where the radio frequency trap 1018 is formed. A coil 1006 connects the two ends of the gap 932 electrically. This coil 1006 forms the inductor of the radio frequency trap 1018. In this embodiment there is a third electrode 1028 which is located inside the cooling line 304 and is under the conductive tube 924 at one end of the gap 932. The third electrode 1028 is capacitively coupled to a section of the conductive tube 924. A wire 1030 then connects the third electrode 1028 to the conductive tube 924 at the other end of the gap 932. The wire 1030 is connected to the conductive tube 924 through a hole 1010 in the cooling line 304.

In the embodiments shown in FIG. 9 and FIG. 10, instead of using a separate radio frequency transmission line and an additional cooling line 304, as normally done in standard ablation catheters, a conducting tube 924 serving both as RF ablation line and as cooling liquid supply. The cooling line 304 and the conductive tube 924 may be the same component. In this case there may be a section of non-conducting or a dielectric tube mounted between the electrodes 926, 928, 1028 and the conductive tube 924 which extends across the gap 932 in the conductive tube 924 of the radio frequency trap 918, 1018. Alternatively, there may be a separate cooling tube which is inside of the conducting tube 924. For the embodiment where a section of non-conducting tubing is used, the coil 906, 1006 of radio frequency trap is wound to the non-conductive junction-tubing.

In FIG. 9, this junction tubing is equipped with two wire 930 connected electrodes 926, 928 on its inner wall, located next to the ends of the tube. The conducting tubes 924 provide some capacitive overlap with those internal plates, which form a distributed capacitor. Symmetric embodiments with two such distributed capacitors are possible as well as an asymmetric version with only a single capacitor at one end of the trap. The common mode currents induced by the incident radio frequency field of the magnetic resonance system on this conductor tube are suppressed by special miniature coaxial radio frequency traps, which are designed such that almost no electric fields leak into the outside of the catheter, especially not into the adjacent tissue. Thus, eventual heating is confined within the trap. Due to the high thermal coupling of the design of this trap in conjunction with the conductive cooling tube, the trap heat can be efficiently dissipated and distributed. Thus local hot spots are completely eliminated and the ablation line becomes radio frequency safe.

In an alternative embodiment such a radio frequency trap can also be designed to be directly integrated into a regular ablation cable. Again, the design is such that the electric fields are confined within the trap and do not leak into the adjacent tissue, so that direct tissue heating is avoided. The standard plastic cooling tube of an irrigated-tip catheter is then used as support for an inductive coil element and serves to cool the radio frequency traps.

Figure 11:
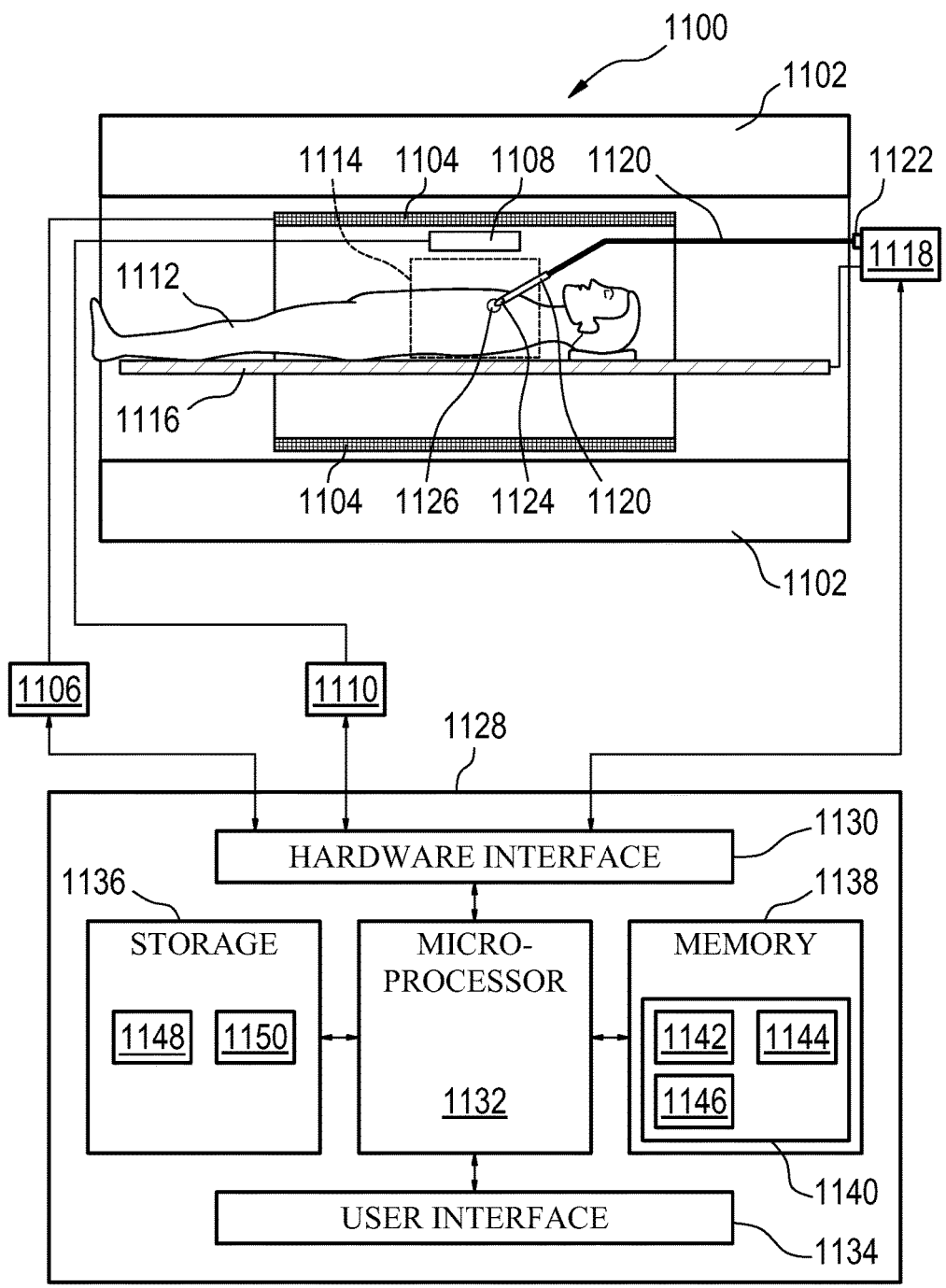
FIG. 11 shows a functional diagram of a magnetic resonance imaging system according to an embodiment of the invention.

In FIG. 11 an embodiment of a magnetic resonance imaging system according to the invention is illustrated. The magnetic resonance imaging system 1100 has a magnet 1102. The magnet 1102 may be a superconducting magnet, a permanent magnet, an electromagnet, or a combination of any of the previous three and is for generating a magnetic field for aligning the spins of nuclei of a subject 1112 within an imaging volume 1114. Inside the bore of the magnet there is also a set of magnetic field gradient coils. The term magnetic field gradient coil refers to one or a collection of coils used for spatial encoding of the magnetic spins of nuclei within the imaging volume. The magnetic field gradient coil 1104 is connected to a magnetic field gradient coil power supply 1106.

Also within the bore of the magnet is a radio frequency coil 1108 which is connected to a radio frequency transceiver 1110. The radio frequency coil 1108 and the radio frequency transceiver 1110 form a radio frequency system which is used for acquiring magnetic resonance data. Also shown in the fig. is a radio frequency ablation catheter 1120. There is a connection 1122 between the radio frequency ablation catheter 1120 and a radio frequency generator 1118. The radio frequency generator 1118 is also shown as being connected to a subject electrode 1116. The subject electrode 1116 forms an electrical connection between the subject 1112 and the radio frequency generator 1118. In this embodiment the subject electrode 1116 also functions as a subject support. At the end of the radio frequency ablation catheter 1120 is shown the tip electrode 1124. When the radio frequency generator 1118 supplies the radio frequency catheter 1120 with radio frequency power, a heating zone 1126 within the subject 1112 is heated.

The radio frequency transceiver 1110, the magnetic field gradient power supply 1106, and the radio frequency generator 1118 are all connected to a hardware interface 1130 of a computer system 1128. The computer system 1128 further comprises a microprocessor 1132 for executing machine executable instructions. The microprocessor is connected to computer storage 1136. The computer storage is storage which is adapted for storing machine executable instructions or machine readable data. Examples of computer storage are but are not limited to a hard drive, a floppy disk, flash memory, or other storage medium. The microprocessor 1132 is also connected to and able to send instructions to a user interface 1134. The user interface 1134 comprises components for receiving input data from an operator and also for displaying information or graphics for an operator. For example the user interface may comprise a keyboard and a mouse.

The user interface 1134 may also comprise a computer display for displaying information and graphics. The user interface may comprise a display 1134 for displaying magnetic resonance images and also plain images a physician or operator can use while guiding the radio frequency ablation catheter 1120 in the subject 1112. The computer system 1128 also comprises computer memory 1138. The computer memory contains machine readable data and machine executable instructions for use by the microprocessor 1132. Stored within the memory 1138 is a computer program product 1140. The computer program product comprises a catheter control module 1142. The catheter control module 1142 comprises machine executable instructions which allow the microprocessor 1132 to control the functionality of the radio frequency generator 1118. The catheter control module 1142 may also control specialized instructions for controlling the operation and ensuring the safety of the radio frequency ablation catheter 1120. For instance if the tip electrode 1124 has a temperature sensor the catheter control module 1142 may contain specialized machine executable instructions which determine if the tip electrode 1124 is abnormally warm due to currents induced in the radio frequency transmission line by the acquisition of magnetic resonance imaging data. For instance during the guiding of the radio frequency ablation catheter, when ablation is not being performed, the acquisition of magnetic resonance imaging data may cause heating of the tip electrode. Secondly, during the use of the radio frequency ablation catheter to ablate tissue, the acquisition of magnetic resonance imaging data may induce currents in the radio frequency transmission line that lead to additional tip electrode 1124 heating. If this additional heating of the tip electrode 1124 in either of these two cases exceeds a predetermined safety threshold, magnetic resonance imaging may be stopped Similarly if the radio frequency generator 1118 contains a reflected power meter for measuring the reflected power of a test frequency that is injected into the radio frequency ablation catheter 1120 there may be specialized code within the catheter control module 1142 which allows microprocessor 1132 to determine if there is a failure of the radio frequency ablation catheter 1120. The computer program product also comprises a magnetic resonance imaging control module 1144 for controlling the functionality of the magnetic resonance imaging system 1100. The computer program product 1140 also comprises an image reconstruction module 1146. The image reconstruction module 1146 contains machine executable instructions for reconstructing magnetic resonance data into magnetic resonance images.

In practice the radio frequency generator 1118 will typically generate radio frequency power at approximately 500 kHz to produce ablation in the subject in the heating zone 126 of the tip electrode. The frequency of the radio frequency traps depends upon the strength of the magnetic field and type of atomic spin which is being measure. For instance, in a 1.5 Tesla field the nuclei of Hydrogen atoms have a resonance frequency of approximately 64 MHz. The large difference in frequency between the Larmour frequency and the frequency used for ablation allows the radio frequency traps to effective filter at the Larmour frequency without a large attenuation at the frequency used to produce ablation.

FIG. 12 shows a section of cooling line 1200 according to an embodiment of the invention. Within the cooling line 1200 is the transmission line 1202. The transmission line 1202 is connected to radio frequency traps 1204. In this embodiment the radio frequency trap 1204 and the transmission line 1202 are both located within the cooling line 1200. By being located within the cooling line 1200 the radio frequency traps 1204 are able to be cooled by forcing a fluid through the cooling line 1200. In this example the radio frequency traps 1204 are constructed on a printed circuit board.

FIG. 13 shows an embodiment of a transmission line according to an embodiment of the invention manufactured using a printed circuit board. A section of cooling line 1200 is also shown in this figure. Instead of having a transmission line which is connected to individual radio frequency traps, the transmission line 1302 and the radio frequency traps are both connected together on the same piece of printed circuit board. The printed circuit board is thin enough so that it is flexible and is bendable. During use as the catheter is manipulated, the printed circuit board is able to twist and bend within the catheter allowing a full range of motion for the catheter.

Figure 14:
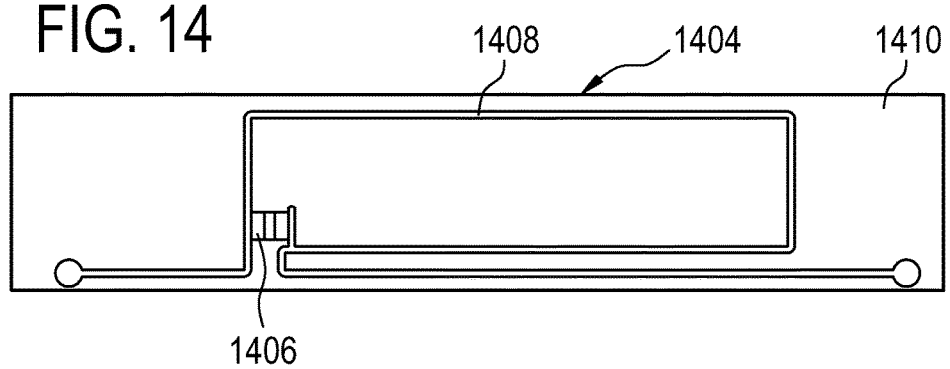
FIG. 14 shows an embodiment according to the invention of a radio frequency trap constructed on a printed circuit board.

FIG. 14 shows an embodiment of a radio frequency trap constructed on a printed circuit board 1410. There is a capacitor 1406 connected in parallel with a coil 1408 patterned on the surface of the printed circuit board 1410. In this example the radio frequency trap 1404 is constructed on a single side of the printed circuit board 1410.

Figure 15:
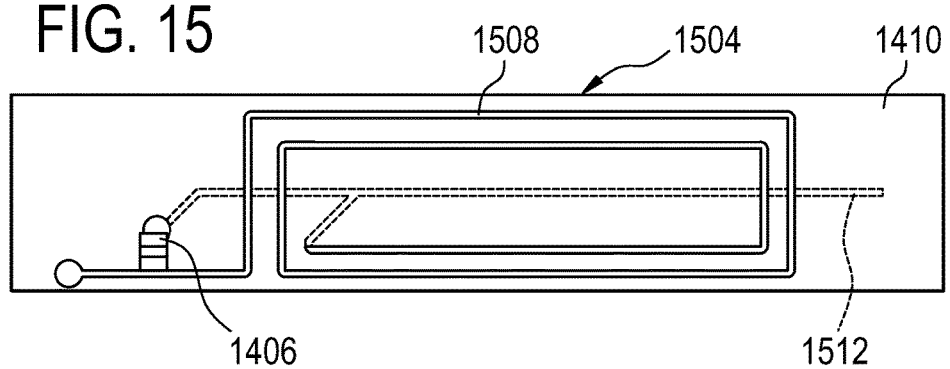
FIG. 15 shows a further embodiment according to the invention of a radio frequency trap constructed on a printed circuit board.

FIG. 15 shows an alternative embodiment of a radio frequency trap 1504 constructed on a printed circuit board 1410. Again a capacitor 1406 is shown in parallel with a coil 1508. In this embodiment the coil 1508 has more than one turn. In order to connect the capacitor 1406 and the coil 1508 a trace 1512 on the opposing side of the printed circuit board 1410 is used.

Figure 16:
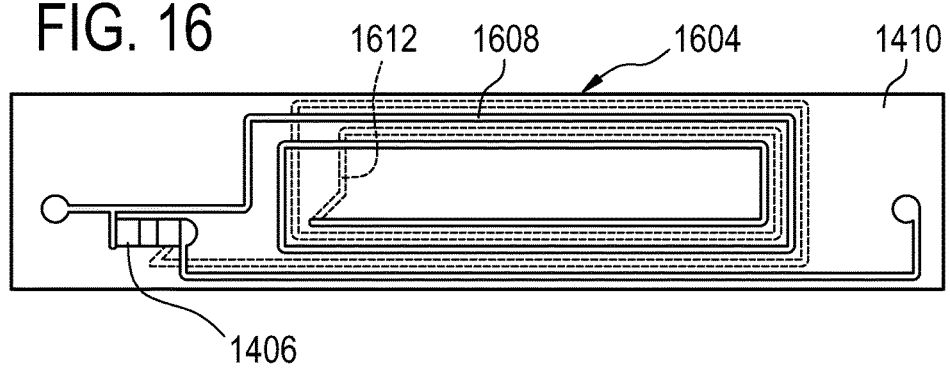
FIG. 16 shows a further embodiment according to the invention of a radio frequency trap constructed on a printed circuit board.

FIG. 16 shows an alternative embodiment of a radio frequency trap 1604 constructed on a printed circuit board 1410. Again a capacitor 1406 is shown in parallel with a coil 1608. The coil 1608 is formed on two layers of the printed circuit board 1410. The section of the coil 1608 is formed on the same side of the printed circuit board as the capacitor 1406. The dashed line 1612 indicates section of the coil formed on the opposing side of the printed circuit board 1410. Forming a portion of the printed circuit board on the opposing side allows a coil 1608 to be formed with a larger number of turns.

Figure 17:
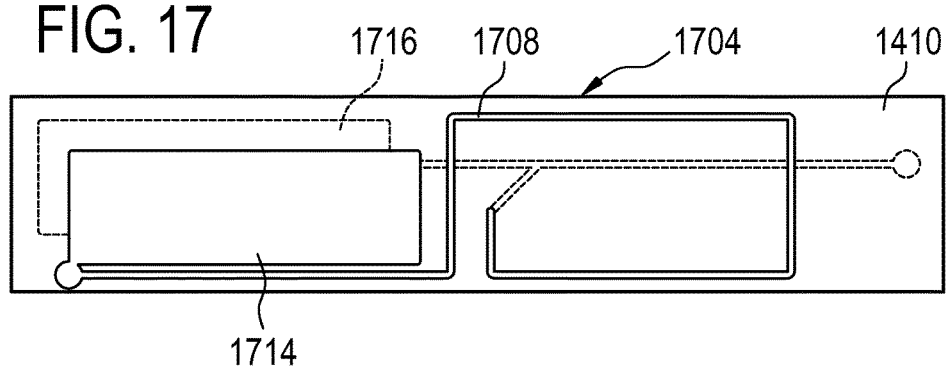
FIG. 17 shows a further embodiment according to the invention of a radio frequency trap constructed on a printed circuit board.

FIG. 17 shows an alternative embodiment of a radio frequency trap 1704 formed on a printed circuit board 1410. In this embodiment a coil 1708 is formed on one side of the printed circuit board 1410. Instead of using a discreet capacitor, capacitive electrodes are formed on opposing sides of the printed circuit board 1410. The printed circuit board 1410 forms the dielectric of the capacitor. The electrode labeled 1714 forms one electrode of the capacitor and the dashed line 1716 indicates an electrode formed on the opposing side of the printed circuit board 1410. In the embodiment shown in FIG. 17 both the capacitor and the coil 1708 are formed on the printed circuit board 1410.

Figure 18:
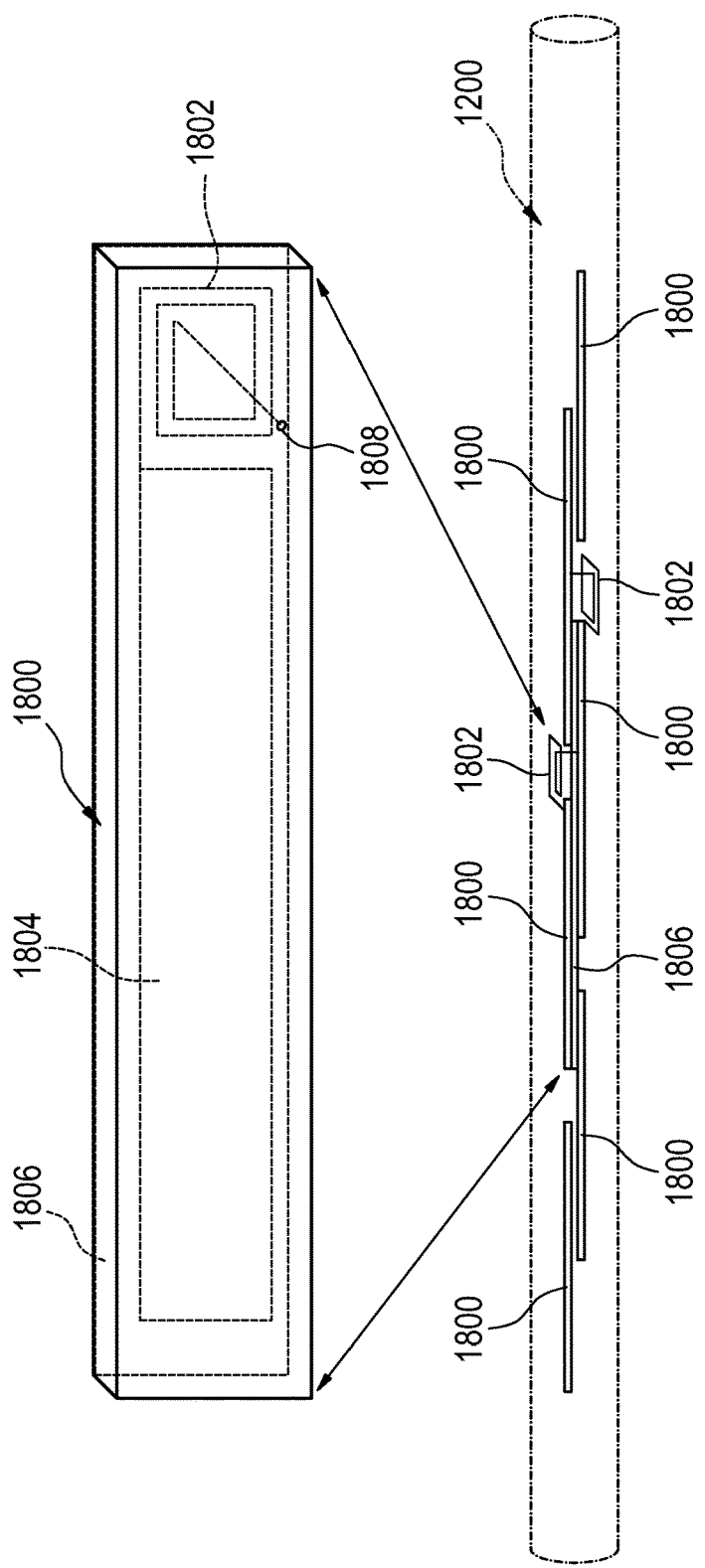
FIG. 18 shows an embodiment according to the invention of a radio frequency transmission line manufactured using multiple printed circuit boards.

FIG. 18 shows a section of cooling line 1200 with an alternative embodiment of a printed circuit board transmission line. The transmission line is formed by sections of individual printed circuit boards 1800. A detailed view of one of the printed circuit boards is shown. Each printed circuit board 1800 has a coil 1802 or inductor which is formed on the surface of the printed circuit board. Additionally each printed circuit board has an electrode 1804 which is also formed on the surface of the printed circuit board 1800. Capacitors are then formed by placing a dielectric layer 1806 between two printed circuit boards 1800. The resonant frequency of the radio frequency trap can be adjusted by adjusting the amount of overlap between two adjacent capacitive electrodes 1804. The sections of printed circuit board 1800 are connected together to form the transmission line for the catheter. There is a through contact 1808 for forming electrical contact between adjacent printed circuit boards 1800.

FIG. 19 shows a section of cooling line 1900 with a transmission line 1902 that has coaxial chokes 1914. The transmission line 1902 is located within the cooling line 1900. The arrows 1912 indicate fluid flow through the cooling line 1900. The coaxial choke 1914 is formed by having a coaxial outer shield 1904 that surrounds the transmission line 1902. There is dielectric material 1906 between the outer shield 1904 and the transmission line 1902. The outer shield is broken into sections. At one end there is a connection 1908 between the outer shield 1904 and the transmission line 1902. The other end of the outer shield 1904 is either not connected to the transmission line 1902 or is connected through a capacitor 1910. When the length of the outer shield 1904 is less than a quarter wavelength of the incident electromagnetic radiation then there will be a very small or no current induced in the transmission line 1902. In this embodiment the outer shield 1904 is cooled by fluid which flows 1912 through the cooling line 1900.

FIG. 20 shows a section of catheter 200 according to an embodiment of the invention. Within the catheter is a section of cooling line 1900. The arrows 1912 indicate fluid flow through the cooling line 1900. Within the cooling line 1900 is an embodiment of a transmission line. In this embodiment there are multiple transmission lines 2002. The multiple transmission lines 2002 are protected from ambient electromagnetic fields by coaxial chokes 1914. In this example the coaxial choke 1914 comprises an outer shield 1904 and an inner shield 2004. The inner shield 2004 is a tube through which the multiple transmission lines 2002 run. Surrounding the inner shield 2004 is a dielectric layer 1906. Surrounding the dielectric layer 1906 is the outer shield 1904. The outer shield 1904 is connected to the inner shield 2004 at point labeled 2008. This is where the connection between the outer shield 1904 and the inner shield 2004 is formed. The other end of the outer shield is either not connected to the inner shield 2004 or is connected to the inner shield through a capacitor 1910. In such a catheter 2000, the structure of the coaxial choke 1914 is repeated periodically. The outer shield 1904 of the coaxial choke 1914 is cooled by fluid flow 1912 through the cooling line 1900.

FIG. 21 shows a further embodiment of a section of cooling line 2102 with a coaxial choke. In this embodiment, the transmission line and cooling line 2102 are combined. The fluid 2104 flows 1912 through the transmission line 2102. The transmission line 2102 in this embodiment is a hollow tube. As with the embodiments shown in FIGS. 19 and 20 a coaxial choke 1914 is formed by an outer shield 1904 which surrounds an inner conductor which is in this case the transmission line 2102. In this embodiment the structure of the coaxial choke 1914 is repeated periodically along the length of the transmission line 2102. One end of the outer shield 1904 is connected to the transmission line 2102 at the point labeled 2108. The other end of the outer shield 1904 is either not connected to the transmission line 2102 or is connected to the transmission line through a capacitor 1910. The space between the outer shield 1904 and the transmission line 2102 may either be filled with a dielectric material 1906 or it may be an air gap. In this embodiment the transmission line 2102 is cooled by the fluid 2104.

FIG. 22 shows an alternative embodiment of a catheter according to an embodiment of the invention. FIG. 22 shows a cross sectional view of the catheter. The outer wall 2000 of the catheter is shown. In this embodiment there is an inner wall 2200. Between the wall of the catheter 2000 and the inner wall 2200 is a region 2202 for fluid flow. The cooling line is the region between the inner wall 2200 and the catheter wall 2000. The arrow labeled 2204 indicates fluid flow through the cooling line. The catheter has an inner cavity 2208 within the inner wall 2200. The circle labeled 2206 indicates a possible location of the transmission line and associated radio frequency traps. In this embodiment the outer shell of the catheter 2000 is cooled so that any heat from the radio frequency traps is carried away before reaching the patient. The transmission line and radio frequency traps may be of any form as was described previously.

Figure 23:
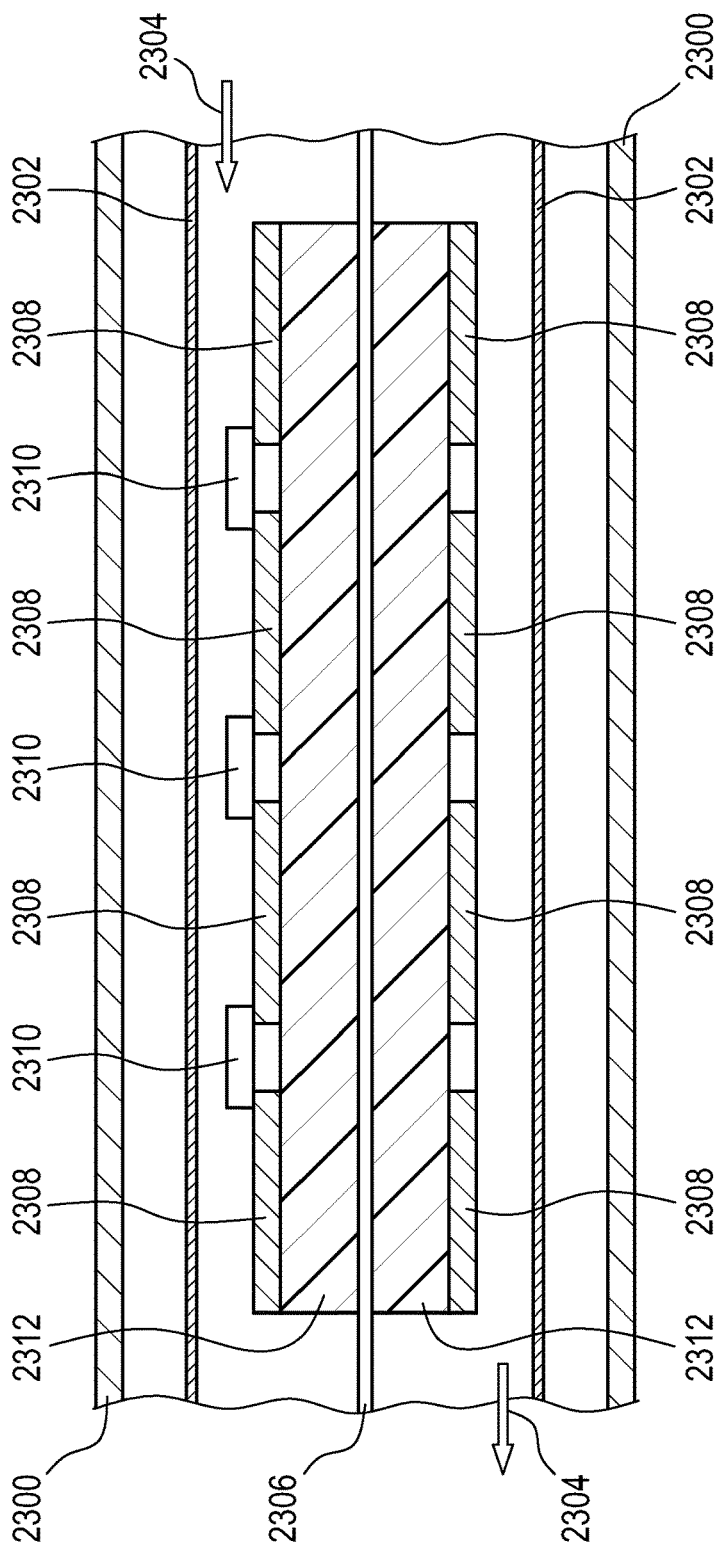
FIG. 23 shows a cross sectional view of a catheter according to a further embodiment of the invention.

FIG. 23 shows a cross sectional view of a short section of a further embodiment of a catheter according to the invention. Shown is the catheter wall 2300. Within the catheter wall 2300 is a section of the cooling line 2302. The arrows 2304 indicate fluid flow within the cooling line 2302. In the embodiment shown in this figure, there is a transmission line 2306 which is shielded by sections of an outer shield 2308. The sections of the outer shield 2308 are connected together by radio frequency traps 2310. The outer shield 2308 is isolated from the transmission line 2306 by a dielectric layer 2312 or other material such as air.

LIST OF REFERENCE NUMERALS

100 Radio frequency ablation catheter
102 Catheter wall

104 Cooling line
106 Radio frequency transmission line
108 Electrode end of radio frequency transmission line
110 Tip electrode
112 Arrow indicating flow of fluid to tip electrode
114 Channel in tip electrode
116 Arrow indicating flow of fluid out of tip electrode channel
118 Radio frequency trap
120 Predetermined distance between adjacent radio frequency traps
200 Radio frequency ablation catheter
202 Temperature sensor
204 High impedance line
210 Tip electrode
212 Arrow indicating fluid flow out of tip electrode channel
214 Channel in tip electrode
216 Cavity formed by catheter wall
302 Equivalent circuit
304 Cooling line
306 Coil
308 Lumped capacitor
310 Holes in cooling line
318 Radio frequency trap
402 Equivalent circuit
406 Coil
408 Lumped capacitor
418 Radio frequency trap
502 Equivalent circuit
506 Coil
508 Distributed capacitor
518 Radio frequency trap
602 Equivalent circuit
606 Coil
618 Radio frequency trap
700 Side view
702 Equivalent circuit
704 Bottom view without cooling line
706 coil
718 Radio frequency trap
720 First electrode
722 Second electrode
724 Electric field lines
800 Side view
802 Equivalent circuit
804 Bottom view without cooling line
806 coil
818 Radio frequency trap
820 First electrode
822 Second electrode
902 Equivalent circuit
906 Coil
918 Radio frequency trap
924 Conductive tube
926 Third electrode
928 Fourth electrode
930 Wire
932 Gap in conductive tube
1002 Equivalent circuit
1010 Hole
1018 Radio frequency trap
1028 Third electrode
1030 Wire
1100 Magnetic resoance imaging system
1102 Magnet
1104 Magnetic field gradient coil
1106 Magnetic field gradient power supply
1108 Radio frequency coil
1110 Radio frequency transceiver
1112 Subject
1114 Imaging zone
1116 Subject electrode
1118 Radio frequency generator
1120 Radio frequency ablation catheter
1122 Connection
1124 Tip electrode
1126 Heating zone
1128 Computer system
1130 Hardware interface
1132 Microprocessor
1134 User interface
1136 Computer storage
1138 Compute memory
1140 Computer program product
1142 Catheter control module
1144 Magnetic resonance imaging control module
1146 Image reconstruction module
1148 Magnetic resonance data
1150 Magnet resonance image
1200 Cooling line
1202 Transmission line
1204 Radio frequency trap
1302 Transmission line
1404 Radio frequency trap
1406 Capcacitor
1408 Coil
1410 Printed circuit board
1508 Coil
1512 Circuit board trace on opposing side of printed circuit board
1800 Printed circuit board
1802 Coil
1804 Capacitive electrode
1806 Dielectric layer
1900 Cooling line
1902 Transmission line
1904 Outer shield
1906 Dielectric
1908 Connection between outer shield and transmission line
1910 Capacitor
1912 Fluid flow through cooling line
1914 Coaxial choke
2000 Wall of catheter
2002 Multiple transmission lines
2004 Inner shield
2008 Connection between outer shield and inner shield
2102 Combined transmission line and cooling line
2104 Fluid
2108 Connection between outer shield and transmission line
2200 Inner wall
2202 Region for fluid flow
2204 Cross indicating fluid flow
2206 Location of transmission line and radio frequency traps
2208 Inner cavity
2300 Catheter wall
2302 Cooling line
2304 Arrow indicating fluid flow
2306 Transmission line
2308 Outer shield
2310 Radio frequency trap
2312 Dielectric layer

The invention claimed is:

1. A catheter comprising:
a dielectric tube configured to pass cooling fluid for cooling a plurality of radio frequency traps with the cooling fluid;
a transmission line, wherein the transmission line comprises a plurality of conductive tube sections separated by gaps, the dielectric tube spanning the gaps;
the plurality of radio frequency traps being along the transmission line, each radio frequency trap including a capacitor and an inductor connected in parallel, the plurality of radio frequency traps being cooled with the cooling fluid in the dielectric tube;
wherein for each gap, the inductor of each respective RF trap includes a coil disposed in the respective gap and connecting adjacent conductive tube sections;
wherein the capacitor includes at least one electrode capacitively coupled with adjacent conductive tube sections, wherein the at least one electrode is mounted inside the dielectric tube and the conductive tube sections are disposed outside the dielectric tube.

2. The catheter of claim 1, wherein the catheter is a radio frequency ablation catheter, wherein the transmission line is a radio frequency transmission line, wherein the catheter further comprises a tip electrode; wherein the dielectric tube is configured to transport the fluid to the tip electrode; wherein the transmission line comprises a connection end and an electrode end; wherein the connection end is adapted to be connected to a radio frequency generator; and wherein the electrode end is connected to the tip electrode.

3. The catheter of claim 2, wherein the tip electrode comprises a temperature sensor.

4. The catheter of claim 1, wherein the plurality of conductive tube sections are spaced apart a distance of less than a wavelength of an RF field of an associated magnetic resonance scanner.

5. The catheter of claim 1, wherein the at least one electrode has a surface area smaller than a surface area of at least one of the conductive tube sections to which it is capacitively coupled.

6. The catheter of claim 1, wherein the coils are disposed within the dielectric tube.

7. The catheter of claim 1, wherein the coils include helical coils concentric with the dielectric tube, the helical coils connecting adjacent conductive tubular sections.

8. A magnetic resonance imaging system comprising:
a catheter according to claim 1;
a magnet adapted for generating a magnetic field for orientating the magnetic spins of nuclei of a subject located within an imaging volume;
a radio frequency system for acquiring magnetic resonance data, wherein the radio frequency system comprises a radio frequency transceiver and a radio frequency coil;
a magnetic field gradient coil for spatial encoding of the magnetic spins of nuclei within the imaging volume;
a magnetic field gradient coil power supply for supplying current to the magnetic field gradient coil;
a subject electrode adapted for forming an electrical connection with the subject;
a radio frequency generator for producing radio frequency power at a first frequency, wherein the radio frequency generator is connected to the subject electrode, and wherein the radio frequency generator is adapted for connecting to the catheter; and
a computer system adapted for constructing images from magnetic resonance imaging data and for controlling the operation of the magnetic resonance imaging system, wherein the computer system is adapted for generating magnetic resonance images of the subject when the radio frequency generator is operational.

9. A magnetic resonance imaging system comprising:
a magnet configured to generate a magnetic field for orientating the magnetic spins of nuclei of a subject located within an imaging volume;
a radio frequency system configured to acquire magnetic resonance data, wherein the radio frequency system comprises a radio frequency transceiver and a radio frequency coil;
a magnetic field gradient coil configured to spatial encode the magnetic spins of nuclei within the imaging volume;
a magnetic field gradient coil power supply configured to supply current to the magnetic field gradient coil;
a subject electrode configured to form an electrical connection with the subject;
a radio frequency generator configured to produce radio frequency power at a first frequency, wherein the radio frequency generator is connected to the subject electrode, and wherein the radio frequency generator is configured to connect to a catheter;
the catheter including a transmission line with a plurality of conductive tubular sections and a plurality of radio frequency traps, the radio frequency traps each comprising an inductor and capacitor connected in parallel and tuned to block the first frequency from propagating along the transmission line, the catheter further including a dielectric cooling tube configured to cool the plurality of radio frequency traps with a fluid,
wherein the conductive tubular sections are disposed around the dielectric cooling tube and separated by gaps, the dielectric cooling tube spanning the gaps;
wherein the inductors include a coil across each gap and connected to adjacent conductive tubular sections to inductively connect the adjacent conductive tubular sections;
wherein the capacitors include capacitor electrodes mounted inside the dielectric tube and configured to capacitively couple the adjacent conductive tubular sections;
a computer system configured to construct images from the magnetic resonance imaging data and to control operation of the magnetic resonance imaging system, wherein the computer system is configured to generate magnetic resonance of the subject when the radio frequency generator is operative.

10. The magnetic resonance imaging system of claim 9, wherein each of the plurality of the gaps is shorter than a quarter wavelength of the first frequency.

11. The magnetic resonance imaging system of claim 9, wherein the radio frequency generator is adapted for generating radio frequency power at a test frequency; wherein the radio frequency generator is adapted for generating the test frequency at a lower power than at the first frequency; wherein the radio frequency generator comprises a reflected power meter for measuring a reflected power at the test frequency; wherein the radio frequency generator is adapted for detecting a malfunction of at least one of the plurality of radio frequency traps using the reflected power; wherein the radio frequency generator is further adapted for signaling the computer system when the malfunction is detected; and wherein the computer system is further adapted for reducing the generation of radio frequency power by the radio frequency transceiver when the computer system is signaled by the radio frequency generator.

12. The magnetic resonance imaging system of claim 9, wherein the radio frequency generator is further adapted for connecting to a temperature sensor; wherein the radio frequency generator is further adapted for determining a temperature measurement of the subject electrode using the temperature sensor; wherein the computer system is further adapted for receiving the temperature measurement from the radio frequency generator; and wherein the computer system is further adapted for reducing the generation of radio frequency power by the radio frequency transceiver when the temperature measurement is above a predetermined safety threshold.

13. A catheter comprising:
- a dielectric tube configured to convey cooling fluid to a catheter tip;
- a plurality of conductive tube sections surrounding the dielectric tube, the plurality of conductive tube sections including a first tube section and a second tube section separated by a gap, the dielectric tube spanning the gap;
- a coil disposed around the dielectric tube in the gap, the coil connecting the first and second conductive tube sections;
- a first electrode capacitively coupled with the first tube section and disposed inside the dielectric tube;
- a conductor connecting the first capacitively coupled electrode with one of the second conductive tube section and a second electrode capacitively coupled to the second conductive tube section;
- wherein the plurality of conductive tube sections define a radio frequency (RF) transmission line including at least one RF trap formed by the coil and one of the first capacitively coupled electrode or the first and second capacitively coupled electrodes, wherein the at least one RF trap is cooled by the cooling fluid.

14. The catheter of claim 13, wherein the catheter is a radio frequency ablation catheter, wherein the catheter tip comprises a tip electrode; wherein the dielectric tube is configured to transport the fluid to the tip electrode; wherein the RF transmission line comprises a connection end and an electrode end; wherein the connection end is adapted to be connected to a radio frequency generator; and wherein the electrode end is connected to the tip electrode.

15. The catheter of claim 14, wherein the tip electrode comprises a temperature sensor.

16. The catheter of claim 13, wherein the plurality of conductive tube sections are spaced apart a distance of less than a wavelength of an RF field of an associated magnetic resonance scanner.

17. The catheter of claim 13, wherein the at least one of the first electrode and the second electrode has a surface area smaller than a surface area of at least one of the conductive tube sections to which it is capacitively coupled.

* * * * *